US010722218B2

(12) United States Patent
Mahfouz

(10) Patent No.: US 10,722,218 B2
(45) Date of Patent: *Jul. 28, 2020

(54) METHOD AND APPARATUS FOR THREE DIMENSIONAL RECONSTRUCTION OF A JOINT USING ULTRASOUND

(71) Applicant: JointVue, LLC, Knoxville, TN (US)

(72) Inventor: Mohamed R. Mahfouz, Knoxville, TN (US)

(73) Assignee: JointVue, LLC, Knoxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/567,873

(22) Filed: Sep. 11, 2019

(65) Prior Publication Data

US 2020/0000436 A1 Jan. 2, 2020

Related U.S. Application Data

(63) Continuation of application No. 15/684,059, filed on Aug. 23, 2017, now Pat. No. 10,512,451, which is a
(Continued)

(51) Int. Cl.
*A61B 8/08* (2006.01)
*A61B 8/00* (2006.01)
(Continued)

(52) U.S. Cl.
CPC .......... *A61B 8/5207* (2013.01); *A61B 5/4504* (2013.01); *A61B 8/0875* (2013.01);
(Continued)

(58) Field of Classification Search
CPC ...................................... G06T 7/564
See application file for complete search history.

(56) References Cited

U.S. PATENT DOCUMENTS

| 6,190,320 B1* | 2/2001 | Lelong ................. G06T 7/0012 600/439 |
| 8,989,460 B2* | 3/2015 | Mahfouz ............... A61F 2/3094 382/128 |
| 2011/0305379 A1* | 12/2011 | Mahfouz ............... A61F 2/3094 382/131 |

FOREIGN PATENT DOCUMENTS

WO WO2010099359 * 9/2010

* cited by examiner

*Primary Examiner* — Luther Behringer
(74) *Attorney, Agent, or Firm* — Dorton & Willis, LLP; Ryan Willis

(57) ABSTRACT

A method of generating a 3-D patient-specific bone model, the method comprising: (a) acquiring a plurality of raw radiofrequency ("RF") signals from an A-mode ultrasound scan of a patient's bone at a plurality of locations using an ultrasound probe that comprises a transducer array; (b) tracking the acquiring of the plurality of raw RF signals in 3-D space and generating corresponding tracking data; (c) transforming each of the plurality of raw RF signals into an envelope comprising a plurality of peaks by applying an envelope detection algorithm to each of the plurality of raw RF signals, each peak corresponding with a tissue interface echo; (d) identifying a bone echo from the tissue interface echoes of each of the plurality of raw RF signals to comprise a plurality of bone echoes by selecting the last peak having a normalized envelope amplitude above a preset threshold, wherein the envelope amplitude is normalized with respect to a maximum peak existing in the envelope; (e) determining a 2-D bone contour from the plurality of bone echoes corresponding to each location of the ultrasound probe to comprise 2-D bone contours; (f) transforming the 2-D bone contours into an integrated 3-D point cloud using the tracking data; and, (g) deforming a non-patient specific 3-D bone model corresponding to the patient's bone in correspon-
(Continued)

dence with the integrated 3-D point cloud to generate a 3-D patient-specific bone model.

18 Claims, 23 Drawing Sheets

Related U.S. Application Data continuation of application No. 13/758,151, filed on Feb. 4, 2013, now abandoned, which is a continuation-in-part of application No. PCT/US2011/046318, filed on Aug. 2, 2011.

(60) Provisional application No. 61/470,952, filed on Apr. 1, 2011, provisional application No. 61/369,848, filed on Aug. 2, 2010.

(51) Int. Cl.
| | | |
|---|---|---|
| *G06T 17/00* | (2006.01) | |
| *A61B 5/00* | (2006.01) | |
| *G06T 19/20* | (2011.01) | |
| *A61B 34/10* | (2016.01) | |
| *A61B 8/14* | (2006.01) | |
| *G06T 7/564* | (2017.01) | |
| *A61B 90/00* | (2016.01) | |
| *A61B 34/20* | (2016.01) | |
| *A61B 5/055* | (2006.01) | |

(52) U.S. Cl.
CPC ............ *A61B 8/4245* (2013.01); *A61B 8/466* (2013.01); *A61B 8/483* (2013.01); *A61B 34/10* (2016.02); *G06T 17/00* (2013.01); *G06T 19/20* (2013.01); *A61B 5/0035* (2013.01); *A61B 5/055* (2013.01); *A61B 8/14* (2013.01); *A61B 8/4263* (2013.01); *A61B 8/4405* (2013.01); *A61B 8/5246* (2013.01); *A61B 2034/105* (2016.02); *A61B 2034/2055* (2016.02); *A61B 2090/367* (2016.02); *A61B 2090/378* (2016.02); *G06T 7/564* (2017.01); *G06T 2210/41* (2013.01); *G06T 2210/56* (2013.01); *G06T 2219/2021* (2013.01)

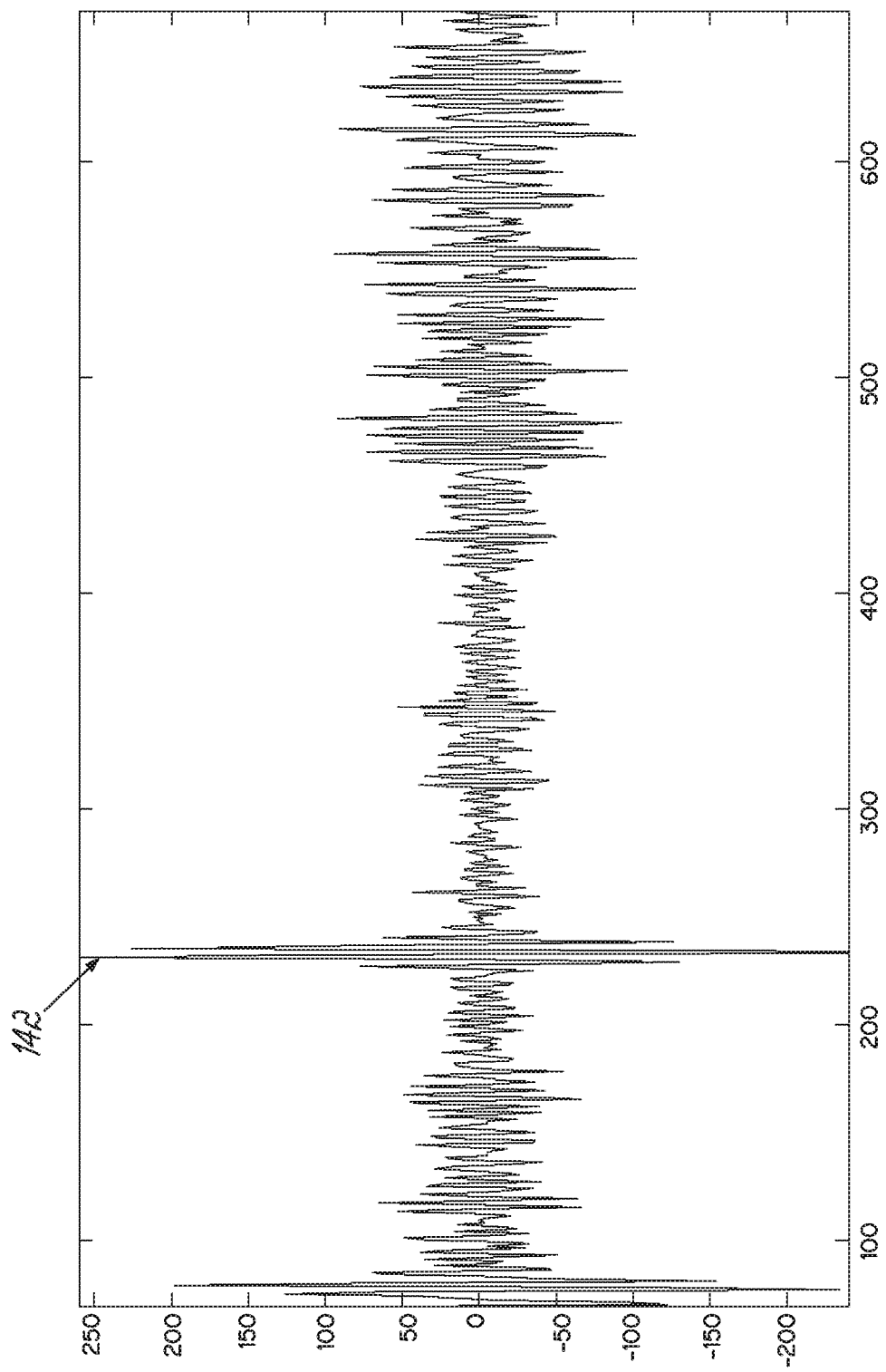

METHOD AND APPARATUS FOR THREE DIMENSIONAL RECONSTRUCTION OF A JOINT USING ULTRASOUND

RELATED APPLICATIONS

This Application is a continuation of U.S. Nonprovisional patent application Ser. No. 15/684,059, filed Aug. 23, 2017, and titled, "METHOD AND APPARATUS FOR THREE DIMENSIONAL RECONSTRUCTION OF A JOINT USING ULTRASOUND," now U.S. Pat. No. 10,512,451, which is a continuation-in-part of U.S. Nonprovisional patent application Ser. No. 13/758,151, filed Feb. 4, 2013, and titled, "METHOD AND APPARATUS FOR THREE DIMENSIONAL RECONSTRUCTION OF A JOINT USING ULTRASOUND," which was a continuation-in-part of Patent Cooperation Treaty Application No. PCT/US11/46318, filed Aug. 2, 2011, and titled, "METHOD AND APPARATUS FOR THREE DIMENSIONAL RECONSTRUCTION OF A JOINT USING ULTRASOUND," which claimed priority to U.S. Provisional Patent Application No. 61/470,952, titled "METHOD AND APPARATUS FOR THREE DIMENSIONAL RECONSTRUCTION OF JOINTS USING ULTRASOUND," filed Apr. 1, 2011, and also claimed the priority to U.S. Provisional Patent Application No. 61/369,848, titled "A NOVEL IMAGING SYSTEM FOR PATIENT-SPECIFIC 3-D KNEE MODEL RECONSTRUCTION USING ULTRASOUND," filed Aug. 2, 2010, the disclosure of each of which is incorporated herein by reference in the entirety.

FIELD OF THE INVENTION

The present invention relates generally to methods of generating 3-D models of musculoskeletal systems and, more particularly, to ultrasound based 3-D bone and cartilage model reconstruction.

BACKGROUND OF THE INVENTION

The reconstruction of a 3-D model for the knee's articulating bones is a key component of computer-aided knee surgery systems. The existence of a pre-operatively acquired model enables the surgeon to pre-plan a surgery by choosing the proper implant size, calculating the femoral and tibial cutting planes, and evaluating the fit of the chosen implant. The conventional method of generating the 3-D model is segmentation of computed tomography ("CT"), or magnetic resonance imaging ("MRI") scans, which are the conventional imaging modalities for creating patient-specific 3-D bone models. The segmentation methods used are either manually, semi-automatic, or fully automated. Although these methods are produce highly accurate models, CT and MRI have inherent draw backs, i.e., both are fairly expensive procedures (especially for the MRI), and CT exposes the patient to ionizing radiation. These limitations have motivated the research of new methods for acquiring and reconstructing bone models.

One alternative method of forming patient-specific models is the use of previously acquired X-Ray images as a priori information to guide the morphing of a template bone model whose projection matches the X-Ray images. Several X-Ray based model reconstruction methodologies have been developed for the femur (including, specifically, the proximal and distal portions), the pelvis, the spine, and the rib cage.

Conventional ultrasound imaging utilizes the B-mode images. B-mode images are constructed by extracting an envelope of received scanned lines of radiofrequency ("RF") signals using the Hilbert transformation. These envelopes are then decimated (causing a drop in the resolution) and converted to grayscale (usually 256 bit) to form the final B-mode image. The conversion to grayscale results in a drop in the dynamic range of the ultrasound data.

The use of ultrasound in computer aided orthopedic surgery has gained a lot of interest in the recent decade due to its relatively low cost and radiation-free nature. More particularly, A-mode ultrasound intra-operative registration has been used for computer aided orthopedic surgery and, in limited cases, in neurosurgery. Ultrasound-MRI registration has been developed utilizing B-mode ultrasound images.

Therefore, it would be desirable to develop a method of utilizing ultrasound techniques to construct 3-D patient-specific bone and cartilage models.

SUMMARY OF THE INVENTION

The present invention overcomes the foregoing problems and other shortcomings, drawbacks, and challenges of high cost or high radiation exposure imaging modalities to generate a patient-specific model by ultrasound techniques. While the present invention will be described in connection with certain embodiments, it will be understood that the present invention is not limited to these embodiments. To the contrary, this invention includes all alternatives, modifications, and equivalents as may be included within the spirit and scope of the present invention.

In accordance with one embodiment of the present invention, a method of generating a 3-D patient-specific bone model is described. The method includes acquiring a plurality of raw radiofrequency ("RF") signals from an A-mode ultrasound scan of the bone, which is spatially tracked in 3D space. The bone contours are isolated in each of the plurality of RF signals and transformed into a point cloud. A 3-D bone model of the bone is then optimized with respect to the point cloud.

According to another embodiment of the present invention, a method for 3-D reconstruction of a bone surface includes imaging the bone with A-mode ultrasound. A plurality of RF signals is acquired while imaging. Imaging of the bone is also tracked. A bone contour is extracted from each of the plurality of RF signals. Then, using the tracked data and the extracted bone contours, a point cloud representing the surface of the bone is generated. A model of the bone is morphed to match the surface of the bone as represented by the point cloud.

In still yet another embodiment of the present invention, a computer method for simulating a surface of a bone is described. The computer method includes executing a computer program in accordance with a process. The process includes extracting a bone contour from each of a plurality of A-mode RF signals. The extracted bone contours are transformed from a local frame of reference into a point cloud in a world-frame of reference. A generalized model of the bone is compared with the point cloud and, as determined from the comparing, the generalized model is deformed to match the point cloud.

Another embodiment of the present invention is directed to a computer program product that includes a non-transitory computer readable medium and program instructions stored on the computer readable medium. The program instructions, when executed by a process, cause the computer program product to isolate a bone contour from a plurality of RF signals. The plurality of RF signals being previously acquired from a reflected A-mode ultrasound beam. The bone contours are then transformed into a point cloud and used to optimize a 3-D bone model of the bone.

Still another embodiment of the present invention is directed to a computing device having a processor and a memory. The memory includes instructions that, when executed by the processor, cause the processor to isolate a bone contour from a plurality of RF signals. The plurality of RF signals being previously acquired from a reflected A-mode ultrasound beam. The bone contours are then transformed into a point cloud and used to optimize a 3-D bone model of the bone.

It is a first aspect of the present invention to provide a method of generating a virtual three dimensional subject-specific musculoskeletal model, the method comprising: (a) generating an envelope for each of a plurality of raw signals obtained from an ultrasound scan of at least a portion of a subject, each envelope including one or more beaks; (b) generating contour lines based on the peaks of the envelopes; (c) transforming the contour lines into a three dimensional (3-D) point cloud using tracking information obtained by tracking a position of an ultrasound transducer during the ultrasound scan of at least the portion of the subject and, (d) optimizing a template tissue model with respect to the point cloud to generate a virtual three dimensional subject-specific musculoskeletal model.

In a more detailed embodiment of the first aspect, the plurality of raw signals includes a first raw signal at a first frequency and a second raw signal at a second frequency, where the first frequency is different than the second frequency. In yet another more detailed embodiment, the method further includes (e) transmitting ultrasound signals during the ultrasound scan; and, (f) obtaining the plurality of raw signals responsive to transmitting the ultrasound signals. In a further detailed embodiment, obtaining the plurality of raw signals comprises: (i) receiving reflected ultrasound energy from each of the transmitted ultrasound signals; and, (ii) converting the reflected ultrasound energy from each of the transmitted ultrasound signals into the plurality of raw signals. In still a further detailed embodiment, transmitting the ultrasound signals comprises: (i) transmitting a plurality of ultrasound pulses each having a frequency; and, (ii) changing the frequency of the ultrasound pulses as the raw signals are acquired. In a more detailed embodiment, the frequency of the ultrasound pulses is changed by sweeping the frequency. In a more detailed embodiment, generating the contour lines based on the peaks of the envelope signals comprises: (i) identifying a first peak of the one or more peaks in each envelope; and, (ii) applying a first filter to the first peaks in temporally adjacent envelopes.

In yet another more detailed embodiment of the first aspect, the first peak is identified in each of the envelopes by using a second filter to estimate an optimal time delay. In yet another more detailed embodiment, the second filter is selected from a group consisting of a Kalman filter, a recursive Bayesian filter, and a particles filter. In a further detailed embodiment, generating the contour lines based on the peaks of the envelopes comprises: (i) calculating a first peak data matrix for the envelope of a first raw signal of the plurality of raw signals; (ii) estimating a second peak data matrix for the envelope of a second raw signal of the plurality of raw signals based on the first peak data matrix; (iii) calculating the second peak data matrix from the envelope of the second raw signal; (iv) calculating an error matrix based on a difference between the estimated second peak data matrix and the calculated second peak data matrix; and, (v) calculating an error correction gain based on the error matrix. In still a further detailed embodiment, the method further includes estimating a third peak data matrix for the envelope of a third raw signal of the plurality of raw signals by multiplying the error matrix by the error correction gain, and adding a product of the multiplication to the calculated second peak data matrix.

In a more detailed embodiment of the first aspect, generating the contour lines based on the peaks of the envelopes comprises: (i) calculating a first peak data matrix for the envelope of a first raw signal of the plurality of raw signals; (ii) generating a first set of particles for each peak in the first peak data matrix; (iii) estimating a second peak data matrix for the envelope of a second raw signal of the plurality of raw signals based on the first set of particles for each peak in the first peak data matrix; (iv) calculating a second peak data matrix for the envelope of the second raw signal; (v) calculating an error matrix based on a difference between the estimated second peak data matrix and the calculated second peak data matrix; (vi) generating a second set of particles for each peak in the second peak data matrix; and, (vii) calculating a weight for each particle in the second set of particles for each peak in the second peak data matrix based on the error matrix. In yet another more detailed embodiment, the method further includes estimating a third peak data matrix for the envelope of a third raw signal of the plurality of raw signals based on the weighted particles of the second set of particles for each peak in the second peak data matrix. In a further detailed embodiment, the first raw signal, the second raw signal, and the third raw signal are temporally adjacent raw signals. In still a further detailed embodiment, transforming the contour lines into the 3-D point cloud includes extracting a 2-D feature from each contour line. In a more detailed embodiment, the contour lines are generated by: (i) applying a statistical weight to each of the one or more peaks in each of the envelopes to create weighted peaks; and, (ii) determining a path of each of the contour lines across the envelopes based on the weighted peaks.

It is a second aspect of the present invention to provide an apparatus for generating a 3-D subject-specific musculoskeletal model, the apparatus comprising: (a) a processor; and, (b) a memory containing instructions that, when executed by the processor, cause the apparatus to: (i) generate an envelope for each of a plurality of raw signals obtained from an ultrasound scan of at least a portion of a subject, each envelope including one or more peaks; (ii) generate contour lines based on the peaks of the envelopes; (iii) transform the contour lines into a three dimensional (3-D) point cloud using tracking information obtained by tracking a position of an ultrasound transducer during the ultrasound scan of at least the portion of the subject and, (iv) optimize a template tissue model with respect to the point cloud to generate a virtual three dimensional subject-specific musculoskeletal model.

BRIEF DESCRIPTION OF THE FIGURES

The accompanying drawings, which are incorporated in and constitute a part of this specification, illustrate embodiments of the present invention and, together with the detailed description of the embodiments given below, serve to explain the principles of the present invention.

FIG. 10A is an example of a raw RF signal as acquired by one transducer of the transducer array of an ultrasound probe.

DETAILED DESCRIPTION OF THE EMBODIMENTS OF THE INVENTION

The various embodiments of the present invention are directed to methods of generating a 3-D patient-specific bone model. To generate the 3-D patient-specific model, a plurality of raw RF signals is acquired using A-mode ultrasound acquisition methodologies. A bone contour is then isolated in each of the plurality of RF signals and transformed into a point cloud. The point clouds may then be used to optimize a 3-D bone model of the bone such that the patient-specific model may be generated.

Figure 1:
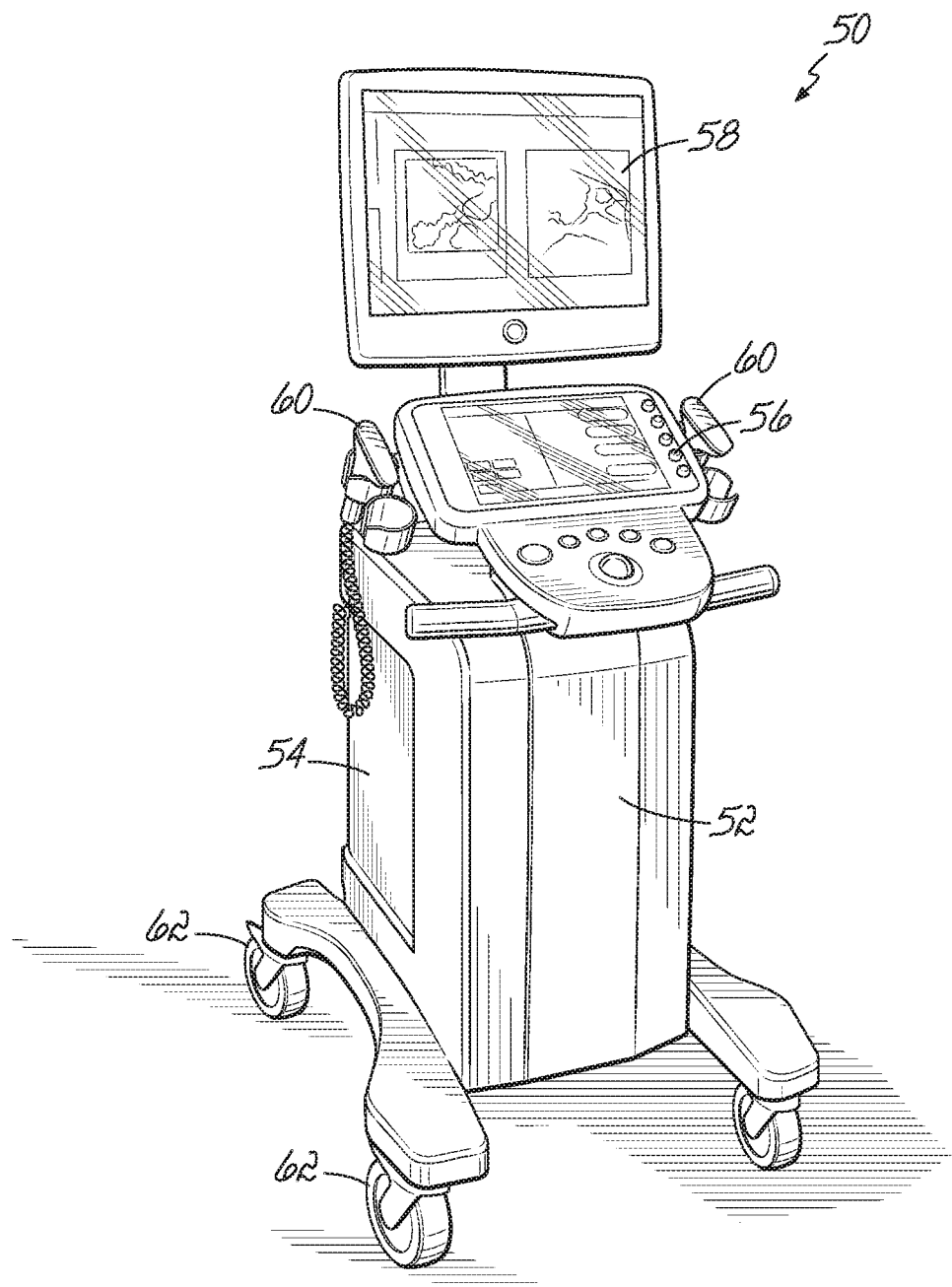
FIG. 1 is a perspective view of an ultrasound instrument in accordance with one embodiment of the present invention.

Turning now to the figures, and in particular to FIG. 1, one embodiment of an ultrasound instrument 50 for use with one or more embodiments of the present invention is shown. The ultrasound instrument 50 should be configurable such that the user may access acquired RF ultrasound data. One suitable instrument may, for example, include the diagnostic ultrasound model SonixRP by Ultrasonix Inc. (Richmond, British Columbia, Canada). The ultrasound instrument 50 includes a housing 52 containing a controller, (for example, a computer 54), an energy or power source (not shown), a user input device 56, an output device (for example, a monitor 58), and at least one ultrasound probe 60. The housing 52 may include caster wheels 62 for transporting the ultrasound instrument 50 within the medical facility.

Figure 2:
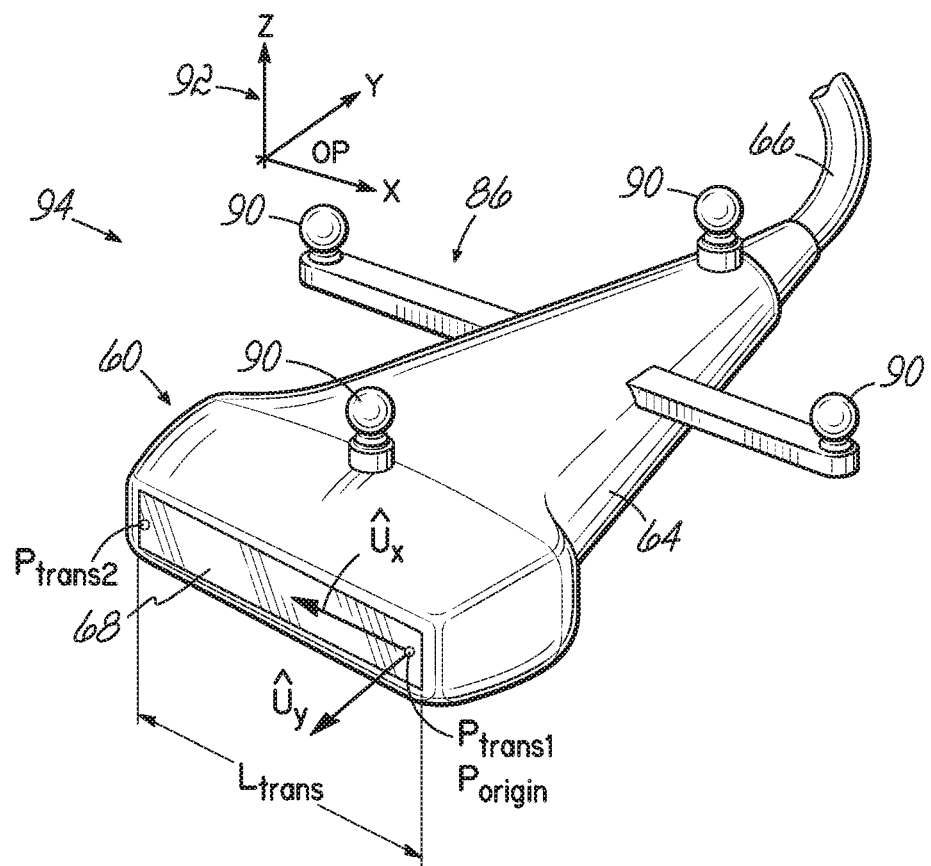
FIG. 2 is a perspective view of a hybrid probe comprising an ultrasound probe and an optical marker, in accordance with one embodiment of the present invention.

The at least one ultrasound probe 60 is configured to acquire ultrasound raw radiofrequency ("RF") signals, and is shown in greater detail in FIG. 2. The ultrasound probe 60, such as the particular embodiment shown, may be a high resolution linear transducer with a center frequency of 7.5 MHz, as is conventionally used in musculoskeletal procedures. The sampling frequency used in digitizing ultrasound echo may be, for example, 20 MHz and must be at least twice the maximum ultrasound frequency. Generally, the ultrasound probe 60 includes a body 64 that is coupled to the ultrasound instrument housing 52 (FIG. 1) by a cable 66. The body 64 further includes a transducer array 68 configured to transmit an ultrasound pulse and to receive reflected ultrasound RF energy. The received RF echo is transmitted along the cable 66, to the computer 54 of the ultrasound instrument 50 (FIG. 1) for processing in accordance with an embodiment of the present invention.

Figure 3:
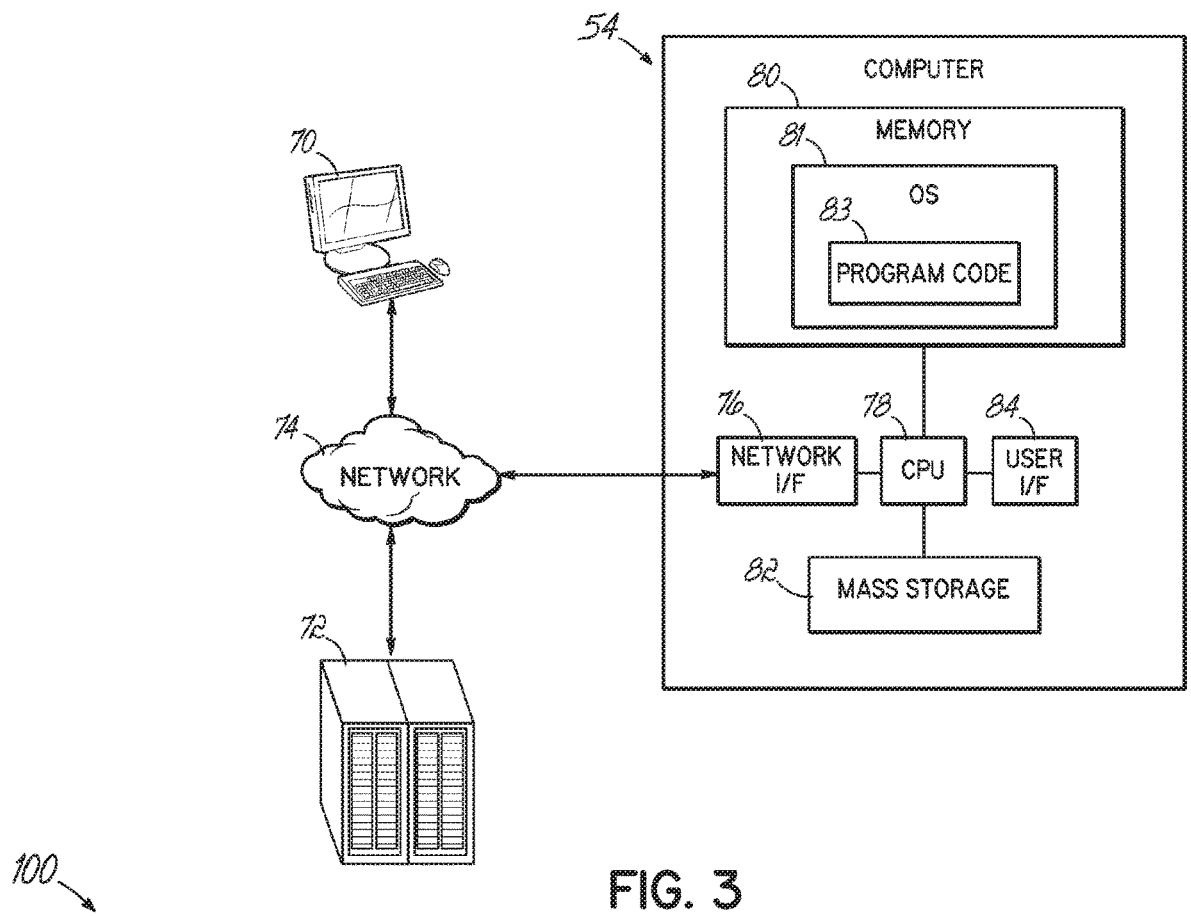
FIG. 3 is a diagrammatic view of a computer system suitable for generating a 3-D patient-specific bone model from A-mode ultrasound RF signals in accordance with one embodiment of the present invention.

The computer 54 of the ultrasound instrument 50 (FIG. 1), as shown in FIG. 3, may be considered to represent any type of computer, computer system, computing system, server, disk array, or programmable device such as multi-user computers, single-user computers, handheld devices, networked devices, or embedded devices, etc. The computer 54 may be implemented with one or more networked computers 70 or networked storage devices 72 using one or more networks 74, e.g., in a cluster or other distributed computing system through a network interface 76 (illustrated as "NETWORK I/F"). For brevity's sake, the computer 54 will be referred to simply as "computer," although it should be appreciated that the term "computing system" may also include other suitable programmable electronic devices consistent with embodiments of the present invention.

The computer 54 typically includes at least one processing unit 78 (illustrated as "CPU") coupled to a memory 80 along with several different types of peripheral devices, e.g., a mass storage device 82, the user interface 84 (illustrated as "User I/F," which may include the input device 56 (FIG. 1) and the monitor 58 (FIG. 1)), and the Network I/F 76. The memory 80 may include dynamic random access memory ("DRAM"), static random access memory ("SRAM"), non-volatile random access memory ("NVRAM"), persistent memory, flash memory, at least one hard disk drive, and/or another digital storage medium. The mass storage device 82 is typically at least one hard disk drive and may be located externally to the computer 54, such as in a separate enclosure or in one or more of the networked computers 70, one or more of the networked storage devices 72 (for example, a server)

The CPU 78 may be, in various embodiments, a single-thread, multi-threaded, multi-core, and/or multi-element processing unit (not shown) as is well known in the art. In alternative embodiments, the computer 54 may include a plurality of processing units that may include single-thread processing units, multi-threaded processing units, multi-core processing units, multi-element processing units, and/or combinations thereof as is well known in the art. Similarly, the memory 80 may include one or more levels of data, instruction, and/or combination caches, with caches serving the individual processing unit or multiple processing units (not shown) as is well known in the art.

The memory 80 of the computer 54 may include an operating system 81 (illustrated as "OS") to control the primary operation of the computer 54 in a manner that is well known in the art. The memory 80 may also include at least one application, component, algorithm, program, object, module, or sequence of instructions, or even a subset thereof, will be referred to herein as "computer program code" or simply "program code," (illustrated as same, 83). Program code 83 typically comprises one or more instructions that are resident at various times in the memory 80 and/or the mass storage device 82 of the computer 54, and that, when read and executed by the CPU 78, causes the computer 54 to perform the steps necessary to execute steps or elements embodying the various aspects of the present invention.

Those skilled in the art will recognize that the environment illustrated in FIG. 3 is not intended to limit the present invention. Indeed, those skilled in the art will recognize that other alternative hardware and/or software environments may be used without departing from the scope of the present invention.

Returning again to FIG. 2, the ultrasound probe 60 has mounted thereto a tracking marker 86, which, for purposes of illustration only, is shown as an optical marker, configured to spatially register the motion of the ultrasound probe 60 during signal acquisition. The tracking marker 86 may be comprised of a plurality of reflective portions 90, which are described in greater detail below. The tracked probe constitutes a hybrid probe 94. In other embodiments, the tracking marker and associated system may be electromagnetic, RF, or any other known 3-D tracking system.

Figure 2A:
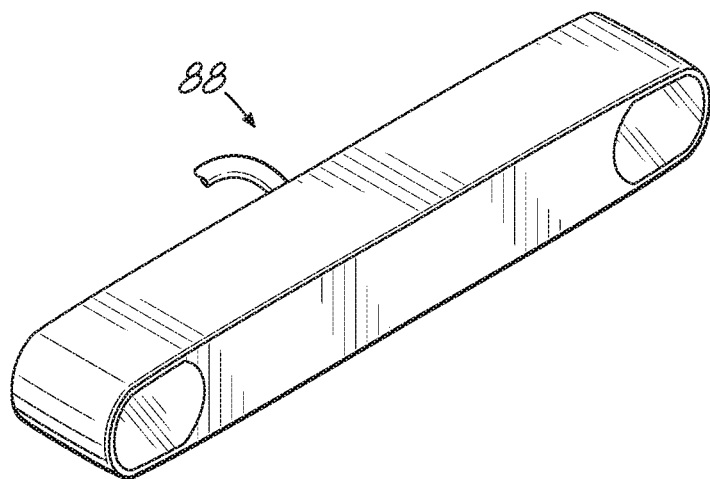
FIG. 2A is a side elevational view of a position sensor for use with the optical marker of the hybrid probe.

The optical marker 86 is operably coupled to a position sensor 88, one embodiment of which is shown in FIG. 2A. In use, the position sensor 88 emits energy (for example, infrared light) in a direction toward the optical marker 86. Reflective portions 90 of the optical marker 86 reflect the energy back to the position sensor 88, which then triangulates the 3-D position and orientation of the optical marker 86. One example of a suitable optical tracking system is the Polaris model manufactured by Northern Digital Inc. (Waterloo, Ontario, Canada).

The optical marker 86 is rigidly attached to the ultrasound probe 60 and is provided a local coordinate frame of reference ("local frame" 92). Additionally, the ultrasound probe 60 is provided another local coordinate frame of reference ("ultrasound frame"). For the sake of convenience, the combination optical marker 86 with the ultrasound probe 60 is referred to as the "hybrid probe" 94. The position sensor 88, positioned away from the hybrid probe 94, determines a fixed world coordinate frame ("world frame").

Operation of the optical tracking system (the optical marker 86 with the position sensor 88) with the ultrasound probe 60, once calibrated, is configured to determine a transformation between the local and ultrasound coordinate frames.

Figure 4:
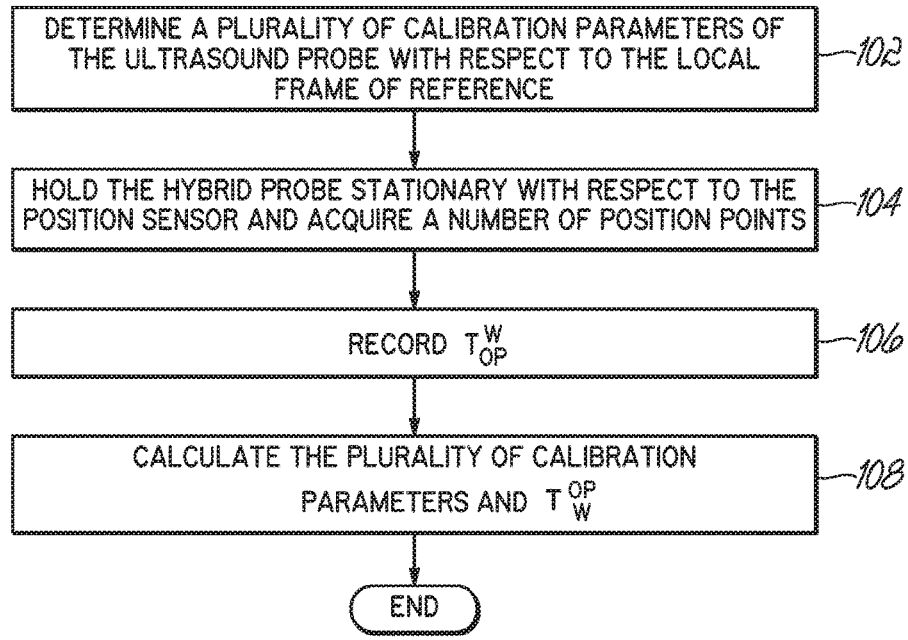
FIG. 4 is a flow chart illustrating one exemplary method of calibrating the optical system and generating a transformation between a local frame and a world frame.

Turning now to FIG. 4, with reference also to FIG. 2, a method 100 of calibrating the optical tracking system according to one embodiment of the present invention is described. To calibrate the optical marker 86 with the position sensor 88, for real-time tracking of the hybrid probe 94, a homogeneous transformation $T_{OP}^{W}$ between the local frame, OP, and the world frame, W, is needed. The calibration method 100 begins with determining a plurality of calibration parameters (Block 102). In the particular illustrative example, four parameters are used and include: $P_{trans-origin}$, i.e., a point of origin on the transducers array 68; $L_{trans}$, i.e., a length of the transducer array 68; $\hat{u}_x$, i.e., a unit vector along the length of the transducer array 68; 4) $\hat{u}_y$, i.e., a unit vector in a direction that is perpendicular to the length of the transducer array 68. These calibration points and vectors are relative to the local frame 92 ("OP").

The hybrid probe is held in a fixed position while the position sensor 88 optical camera acquires a number of position points, including, for example: $P_{trans1}$, i.e., a first end of the transducer array 68; $P_{trans2}$, i.e., a second end of the transducer array 68; and $P_{plane}$, i.e., a point on the transducer array 68 that is not collinear with $P_{trans1}$ and $P_{trans2}$ (Block 104). The homogeneous transformation between OP and W, $T_{OP}^{W}$, is the recorded (Block 106). The plurality of calibration parameters are then calculated (Block 108) from the measured number of points and the transformation, $T_{OP}^{W}$, as follows:

$$T_W^{OP} = (T_{OP}^W)^{-1} \tag{1}$$

$$P_{trans-origin} = T_W^{OP} P_{trans1} \tag{2}$$

$$L_{trans} = \|P_{trans2} - P_{trans1}\| \tag{3}$$

$$\hat{u}_x = T_W^{OP} \frac{P_{trans2} - P_{trans1}}{\|P_{trans2} - P_{trans1}\|} \tag{4}$$

$$\hat{u}_y = \frac{(P_{plane} - P_{trans1}) \times (P_{trans2} - P_{trans1})}{\|(P_{plane} - P_{trans1}) \times (P_{trans2} - P_{trans1})\|} \tag{5}$$

With the plurality of calibration parameters determined, the hybrid probe 94 may be used to scan a portion of a patient's musculoskeletal system while the position sensor 88 tracks the physical movement of the hybrid probe 94.

Figure 5C:
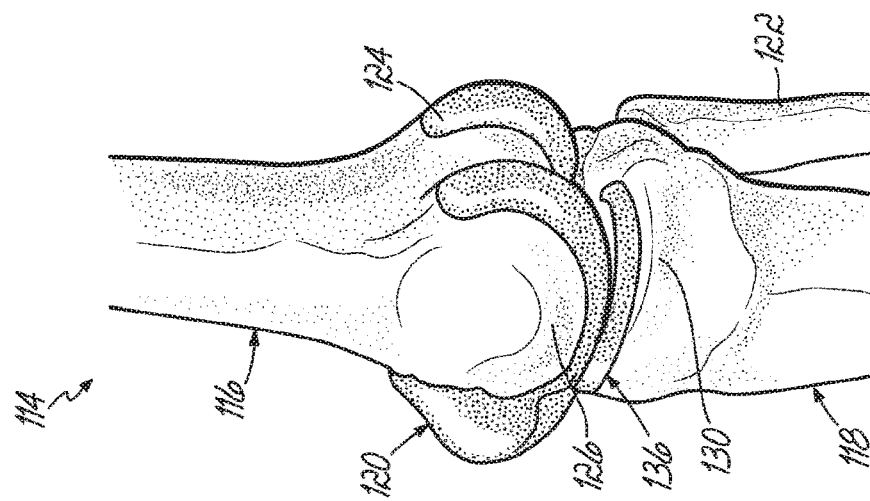
FIGS. 5A-5C are diagrammatic views of a knee joint, showing the anterior, the medial, and the posterior portions, respectively.
Figure 5B:
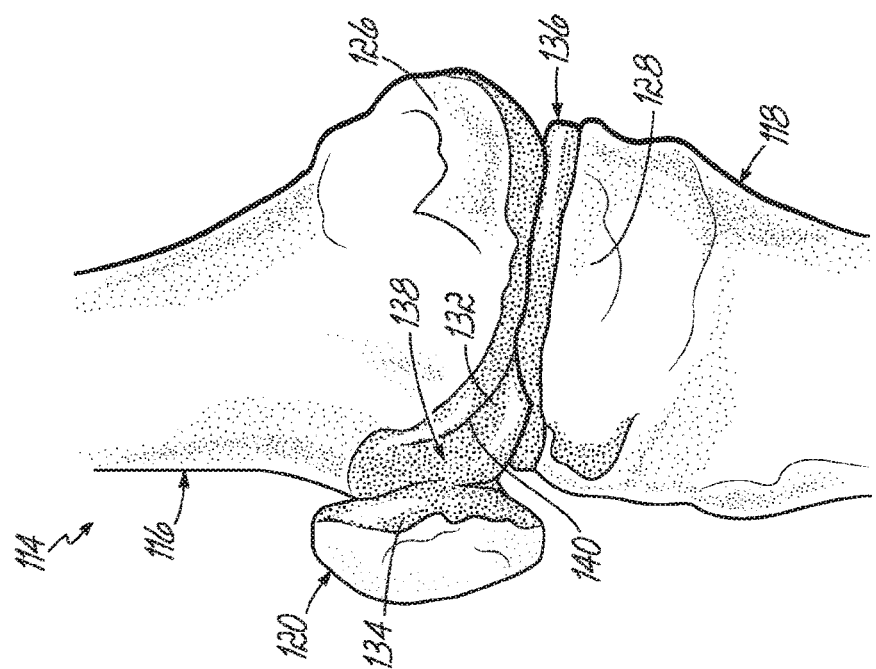
Figure 5A:
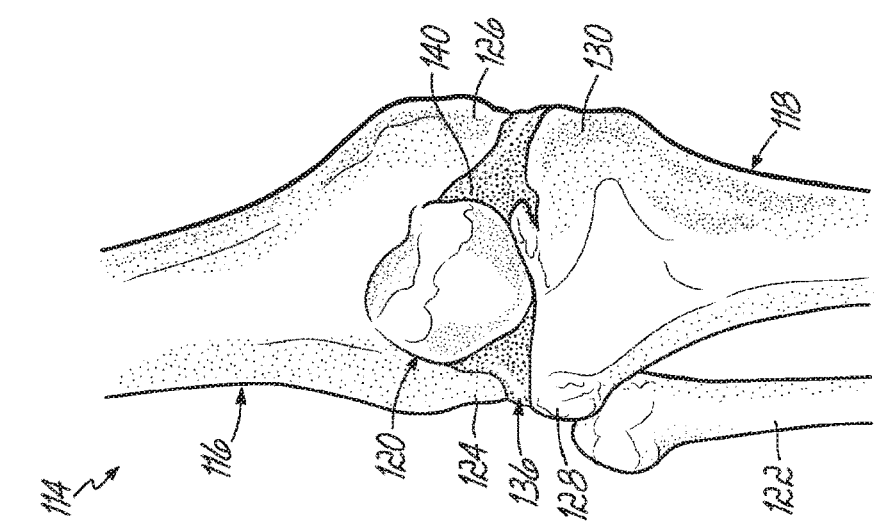
Figure 6A:
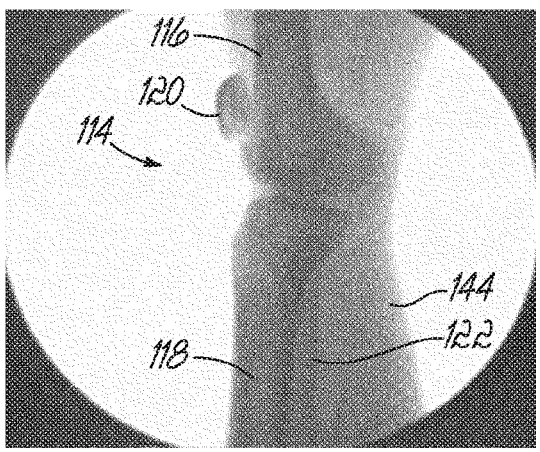
FIGS. 6A-6F are fluoroscopic images of the knee joint in a plurality of degrees of flexion.
Figure 6B:
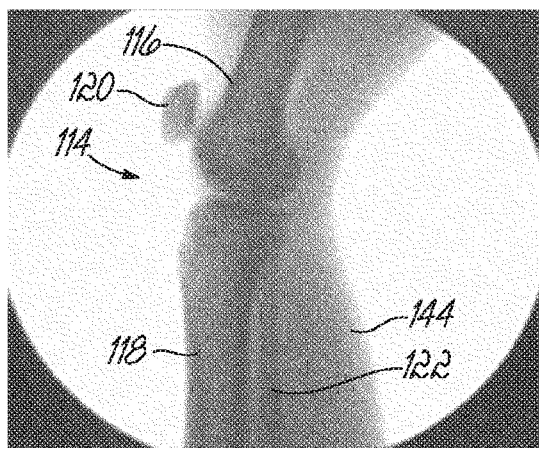
Figure 6C:
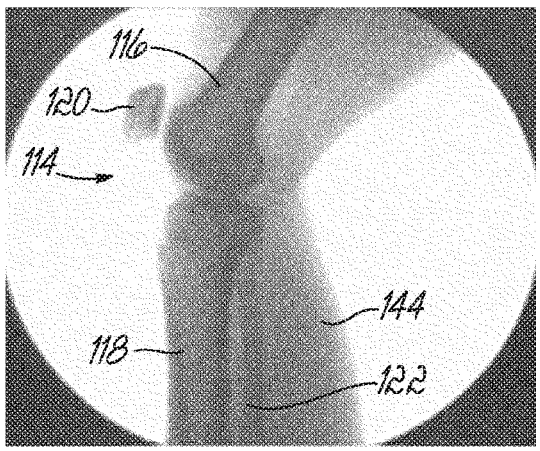
Figure 6D:
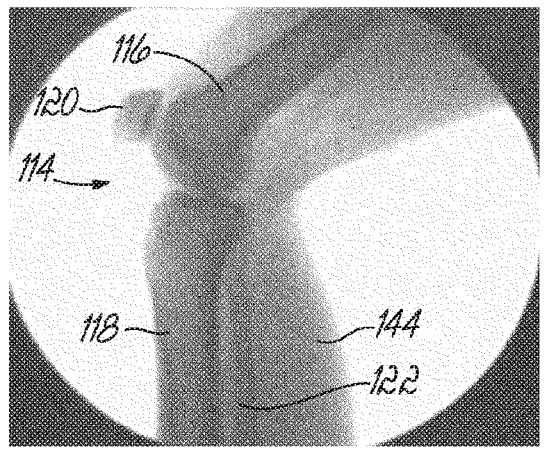
Figure 6E:
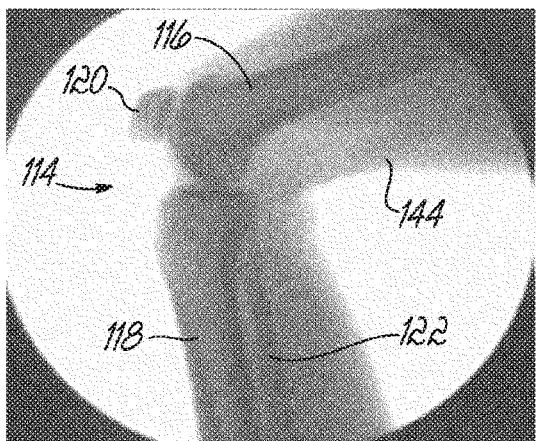
Figure 6F:
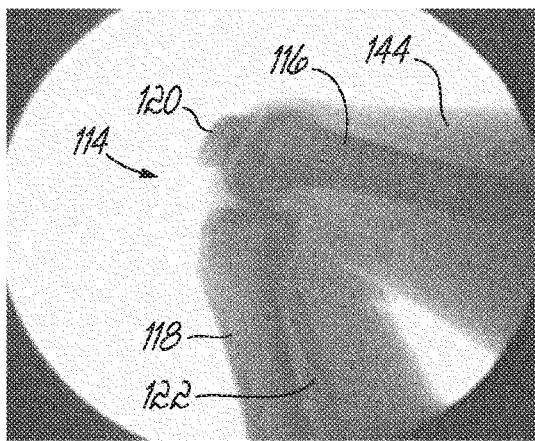

Because of the high reflectivity and attenuation of bone to ultrasound, ultrasound energy does not penetrate bone tissues. Therefore, soft tissues lying behind bone cannot be imaged and poses a challenge to ultrasound imaging of a joint. For example, as shown in FIGS. 5A-5C, the knee joint 114 is formed of three articulating bones: the femur 116, the tibia 118, and the patella 120, with the fibula 122 shown as environment. These bones 116, 118, 120 articulate together in two sub-joints: (1) the tibio-femoral joint 136 is formed by the articulation of the femur 116 with the tibia 118 at the respective condyles 124, 126, 128, 130 and (2) the patello-femoral joint 138 is formed by the articulation of the patella 120 with the femur 116 at the patellar surface 132 of the femur 116 and the articular surface 134 of the patella 120. During flexion-extension motions of the knee joint 114, portions of one or more articulating surfaces of the bones 116, 118, 120 are visible to the ultrasound beam, while other articulating surfaces are occluded. FIGS. 6A-6F include various fluoroscopic images of one patient's knee joint 114, showing the articulating surfaces at a plurality of degrees of flexion.

To acquire ultrasound images of a majority of the articulating surfaces, at least two degrees of flexion are required, including, for example, a full extension (FIG. 6A) and a deep knee bend (FIG. 6F) (or 90° flexion (FIG. 6E) if a deep knee bend is too difficult for the patient to achieve). That is, when the knee joint 114 is in the full extension (FIG. 6A), the posterior portions of the distal femur 116 and the proximal tibia 118 are accessible to the ultrasound beam. When the knee joint 114 is in the deep knee bend (FIG. 6F), the anterior surface of the distal femur 116, the trochlear grove 140, most of the inferior surface of the femoral condyles 124, 126, the anterior superior surface of the tibia 118, and the anterior surface of the tibia 118 are accessible to the ultrasound beam. Both the medial and lateral parts of the femur 116 and tibia 118 are visible at all flexion angles of the knee joint 114.

Figure 7:
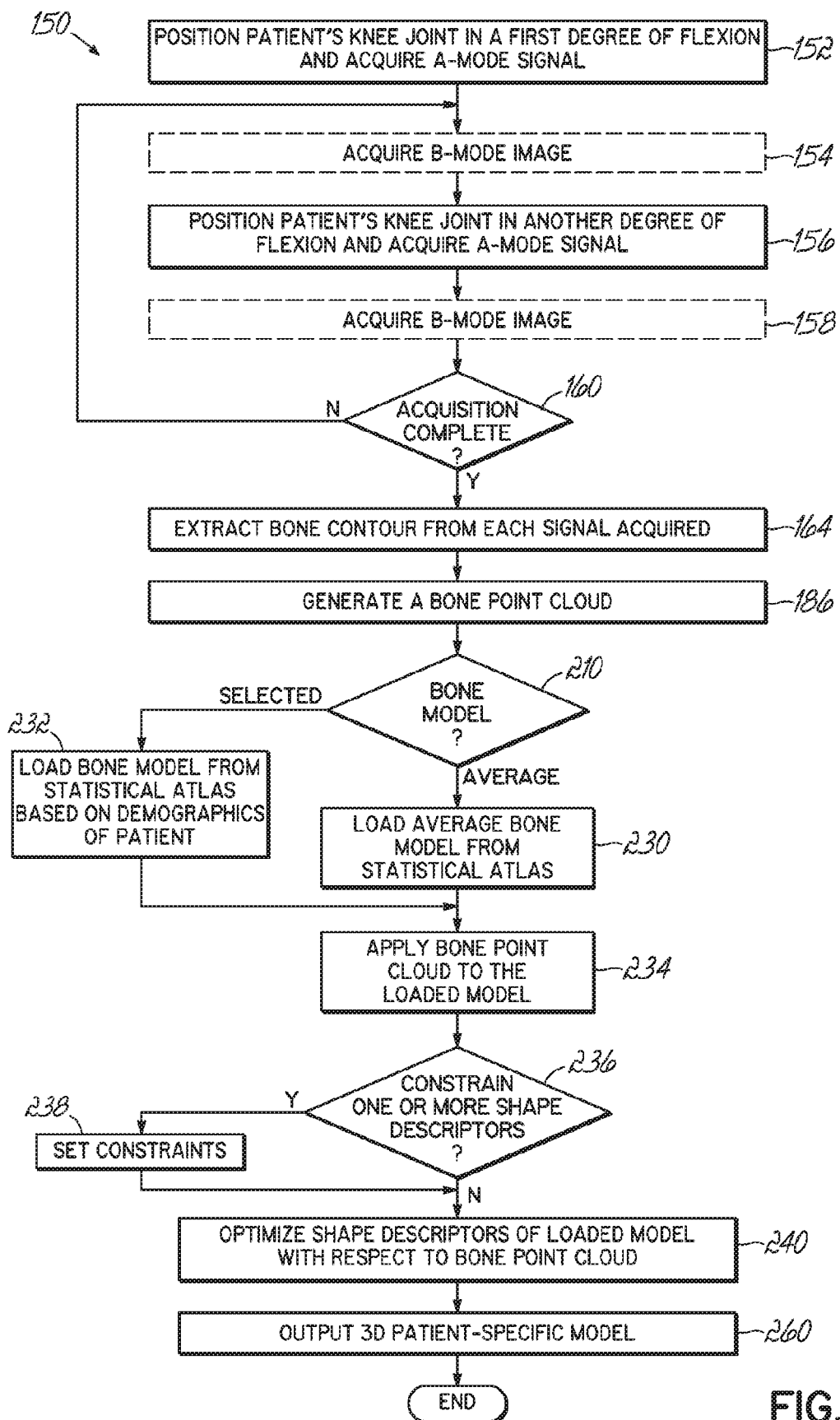
FIG. 7 is a flow chart illustrating one exemplary method of acquiring A-mode ultrasound RF signal and generating the 3-D patient-specific bone model.
Figure 8:
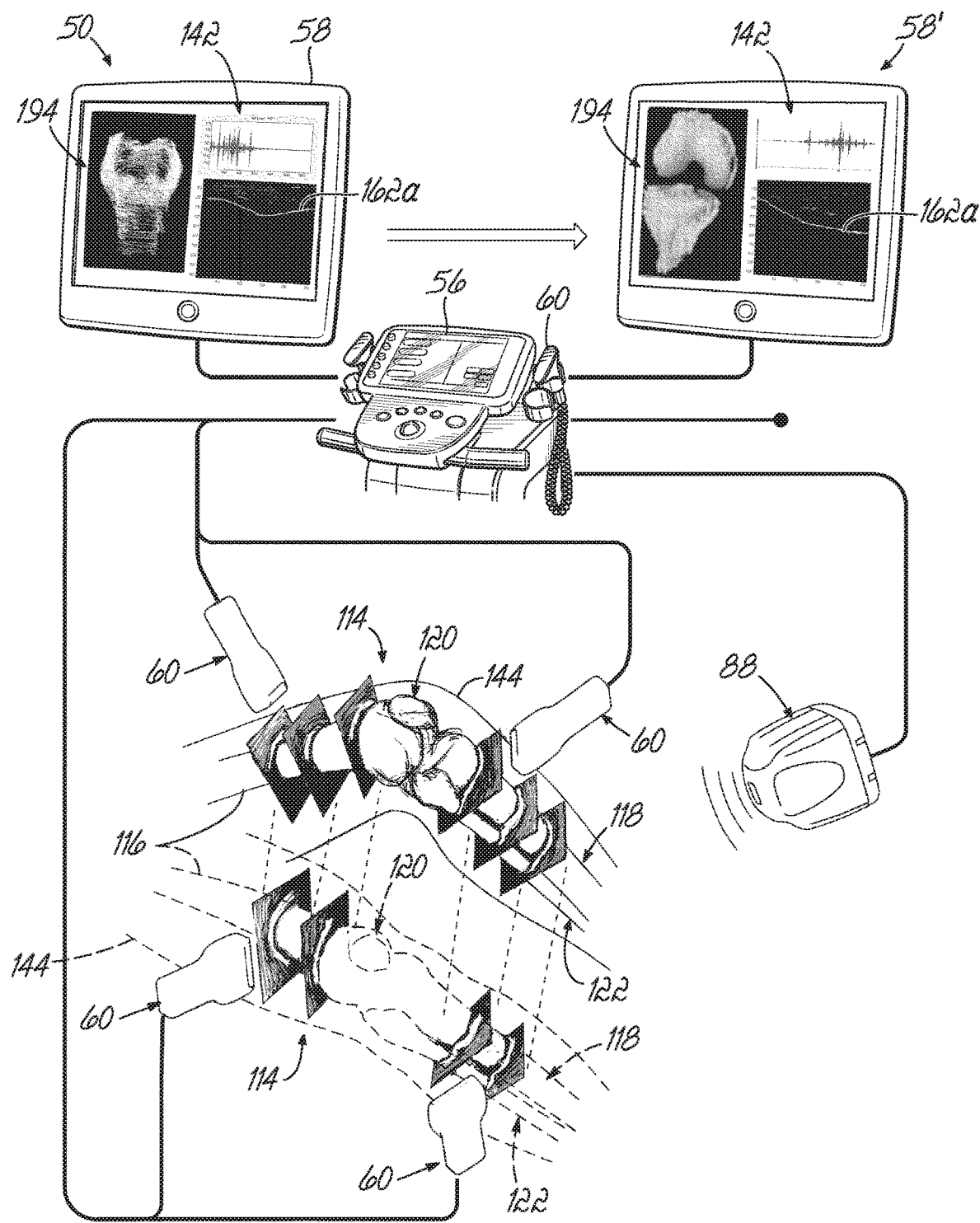
FIG. 8 is a diagrammatic view of the method of acquiring A-mode ultrasound RF signals in accordance with FIG. 7.

Turning now to FIG. 7, one method 150 of acquiring data for construction of a 3-D patient-specific bone model is described. The method begins with acquiring a plurality of RF signals from an A-mode ultrasound beam scan of a bone. To acquire the RF signals for creating the 3-D patient-specific model of the knee joint 114, the patient's knee joint 114 is positioned and held in one of the two or more degrees of flexion (Block 152). The hybrid probe 94 is positioned, at two or more locations, on the patient's epidermis 144 adjacent to the knee joint 114 for acquisition of the A-mode RF signal 142, one example, as shown in FIG. 8. Although the acquired signal includes a plurality of RF signals, for convenience, the RF signals are sometimes referred to herein in singular form.

Figure 9:
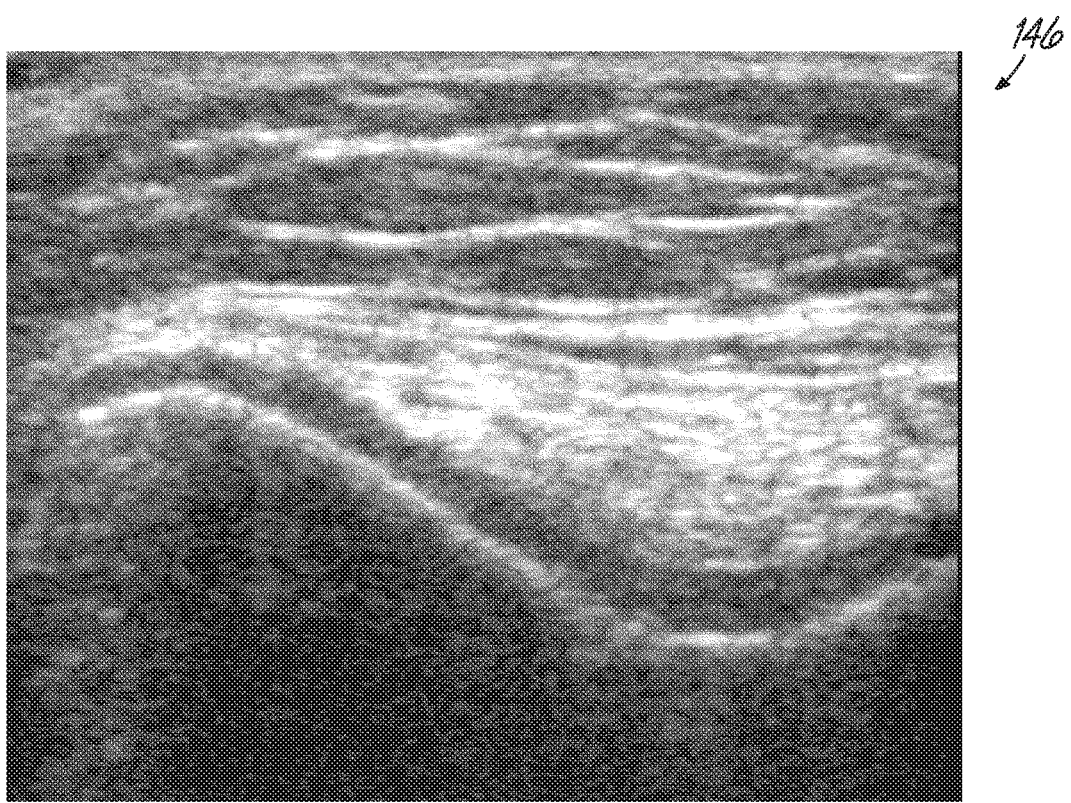
FIG. 9 is a B-mode ultrasound image of a knee joint, which may optionally be shown from the A-mode ultrasound RF signal.

As shown in FIG. 8, with reference also to FIG. 7, the position of the patient's knee joint 114 is held stationary to avoid motion artifacts during image acquisition. Should motion occur, scans may be automatically aligned to the statistically-most likely position given the data acquired. Furthermore, holding the knee stationary and compensating for movement removes the need for invasive fiducial bone markers or high-error skin markers. In some embodiments, B-mode images, similar to the one shown in FIG. 9, may also be processed from the gathered data (Block 154) for subsequent visualization and overlain with the bone contours, as described in detail below.

When the RF signal 142, and if desired B-mode image, acquisition is complete for the first degree of flexion, the patient's knee 114 is moved to another degree of flexion and the reflected RF signal 142 acquired (Block 156). Again, if desired, the B-mode image may also be acquired (Block 158). The user then determines whether acquisition is complete or whether additional data is required (Block 160). That is, if visualization of a desired surface of one or more bones 116, 118, 120 is occluded ("NO" branch of decision block 160), then the method returns to acquire additional data at another degree of flexion (Block 156). If the desired bone surfaces are sufficiently visible ("YES" branch of decision block 160), then the method 150 continues.

FIG. 8 illustrates acquisition of the RF signal 142 in yet another manner. That is, while the patient's leg is in full extension (shown in phantom), the hybrid probe 94 is positioned at two or more locations on the patient's epidermis 144 adjacent to the knee joint 114. The patient's leg is then moved to a second degree of flexion (90° flexion is shown in solid) and the hybrid probe 94 again positioned at two or more locations on the patient's epidermis 144. All the while, the position sensor 88 tracks the location of the hybrid probe 94 in the 3-D space. Resultant RF signal profiles, bone models, bone contours, and so forth may be displayed on the monitor 58 during and the monitor 58' after the model reconstruction.

Figure 10B:
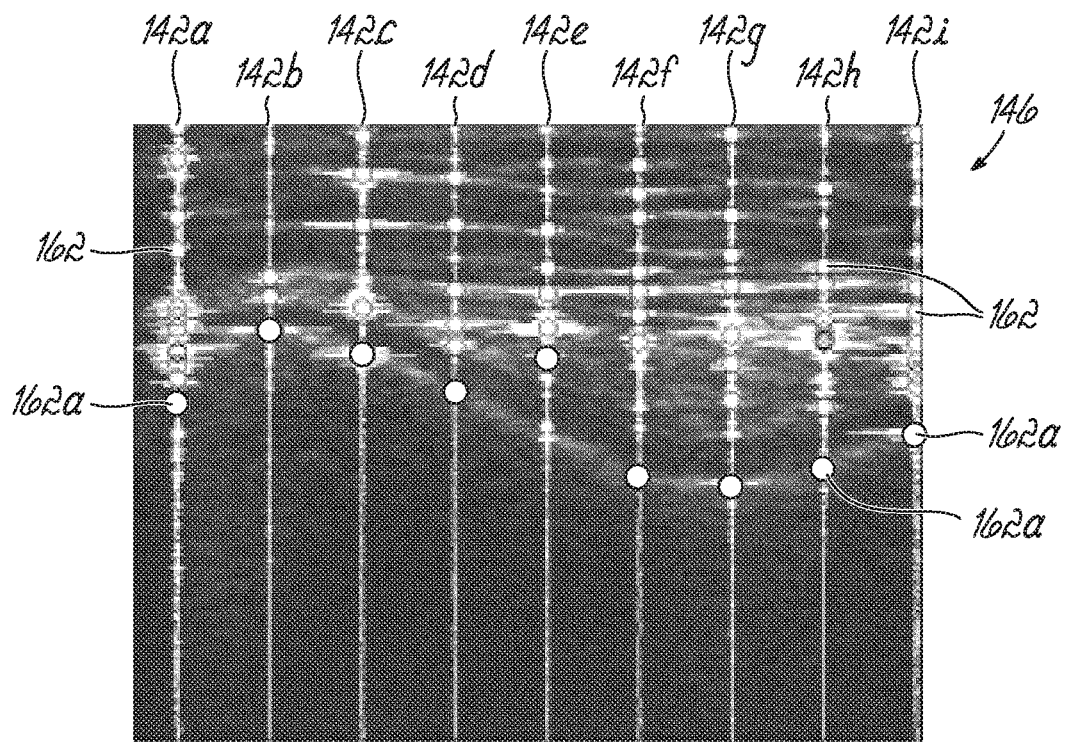
FIG. 10B is the ultrasound frame illustrates select ones of the RF signals overlaid the B-mode ultrasound image of FIG. 9.
Figure 16B:
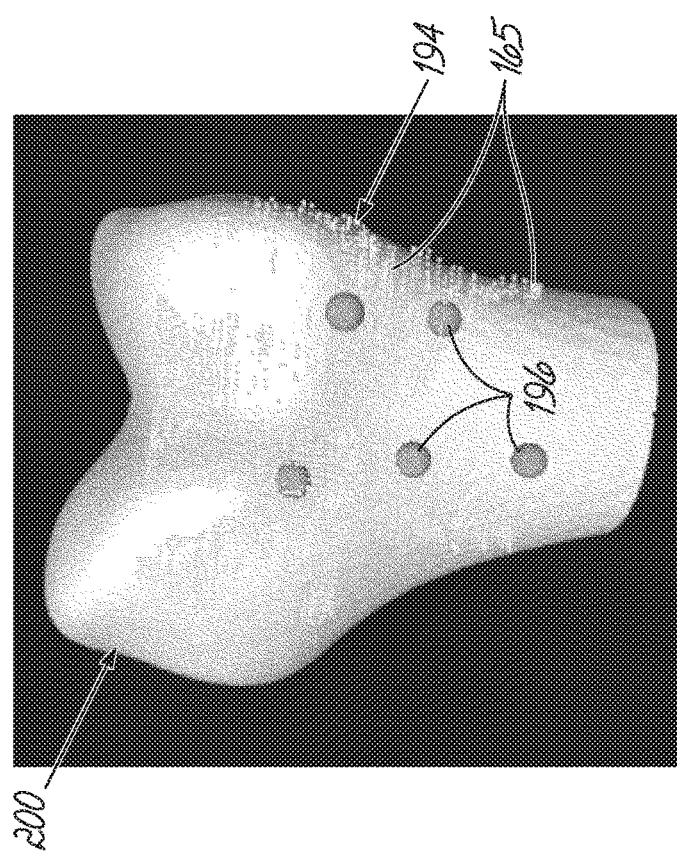
FIGS. 16B, 16D, 17B, and 17D are examples in which the bone point clouds of FIGS. 16A, 16C, 17A, and 17C, respectively, are aligned to a bone model.
Figure 16A:
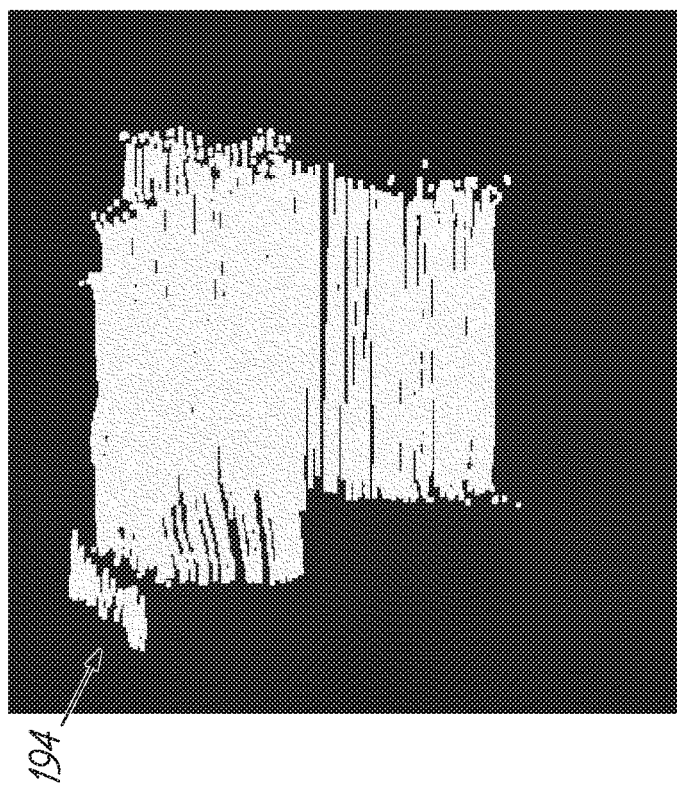
FIGS. 16A, 16C, 17A, and 17C are exemplary bone point clouds, generated in accordance with one embodiment of the present invention.
Figure 16D:
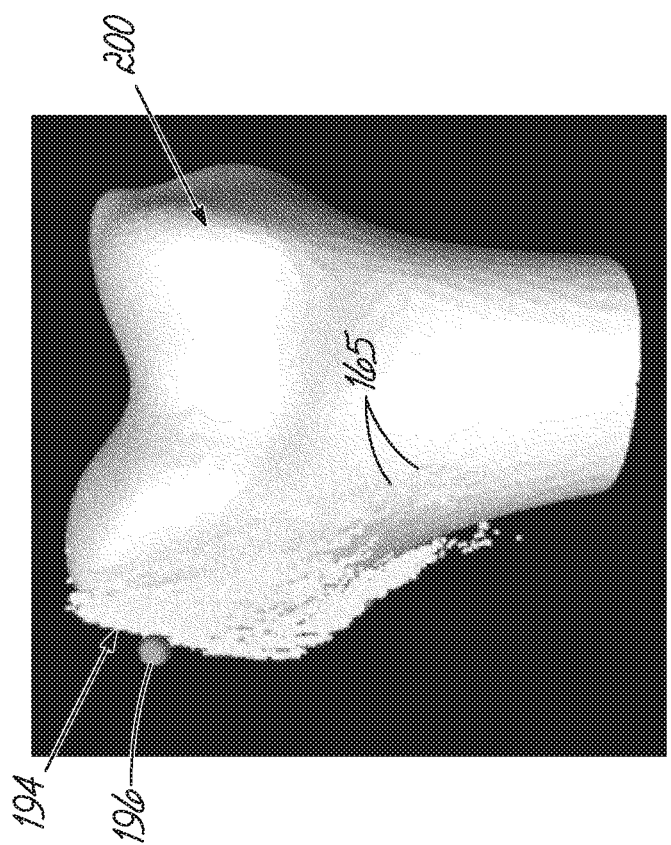
Figure 16C:
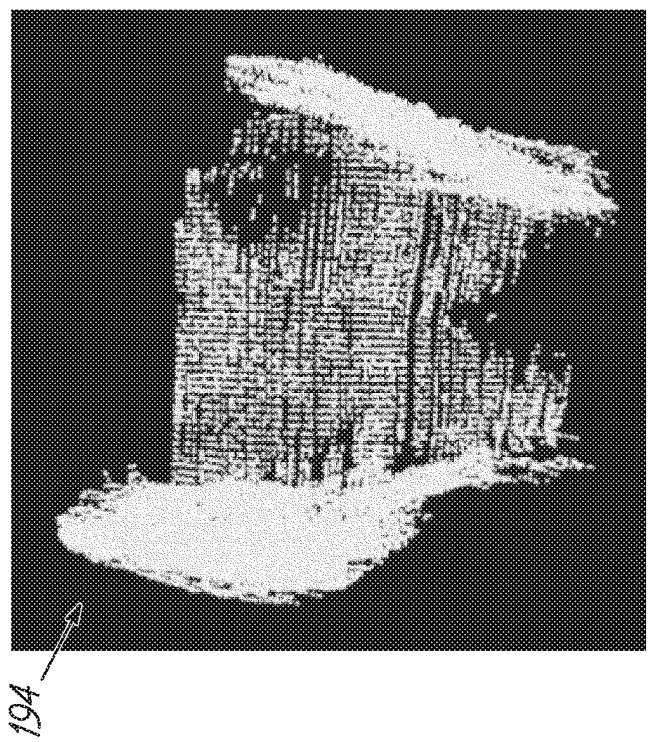
Figure 17B:
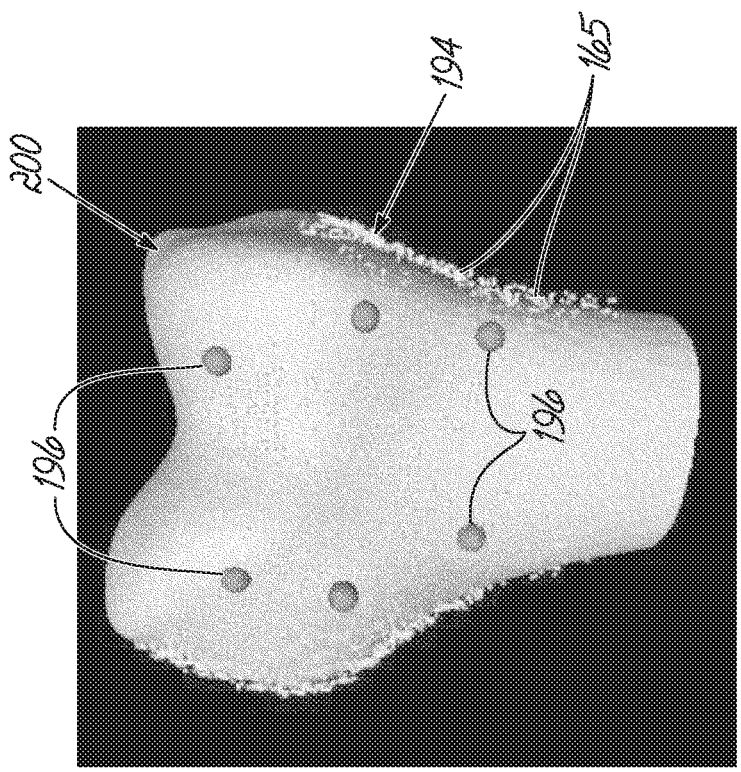
Figure 17A:
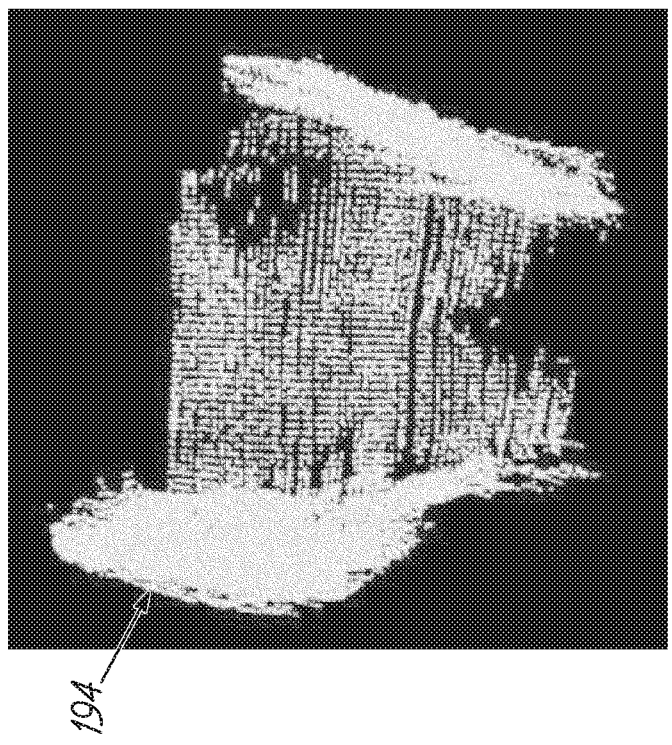
Figure 17D:
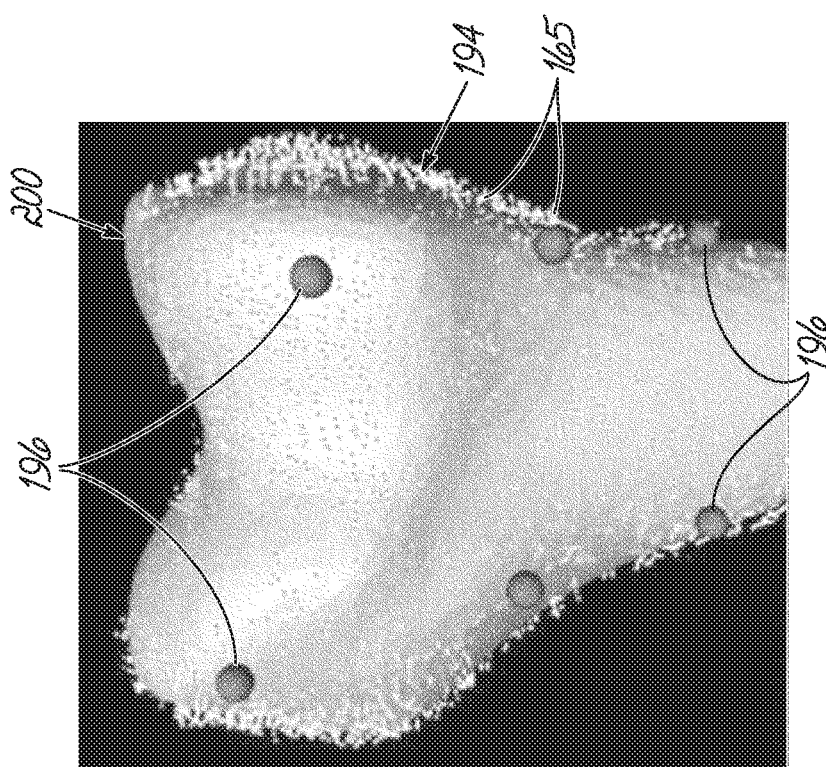
Figure 17C:
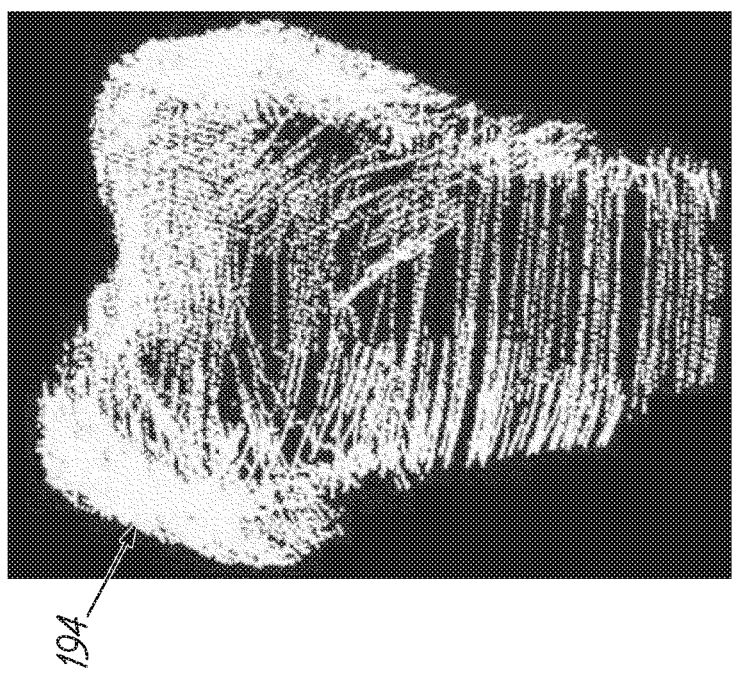

After all data and RF signal acquisition is complete, the computer 54 (FIG. 3) is operated to automatically isolate that portion of the RF signal, i.e., the bone contour, from each of the plurality of RF signals. In that regard, the computer 54 (FIG. 3) may sample the echoes comprising the RF signals to extract a bone contour for generating a 3-D point cloud 165 (FIG. 16B) (Block 164). More specifically, and with reference now to FIGS. 10A-10E and 11, with continued reference to FIGS. 7-9, one method 164 of extracting the bone contours from each of the RF signal 142 is shown. FIG. 10A illustrates one exemplary, raw RF signal 142 as acquired by one transducer comprising the transducer array 68 (FIG. 2) of the ultrasound probe portion of the hybrid probe 94 (FIG. 2). Each acquired raw, RF signal includes a number of echoes 162, wherein the echoes 162 may be isolated, partially overlapping, or fully overlapping. Each of the plurality of echoes originates from a reflection of at least a portion of the ultrasound energy at an interface between two tissues having different reflection and/or attenuation coefficients, as described in greater detail below.

Figure 10C:
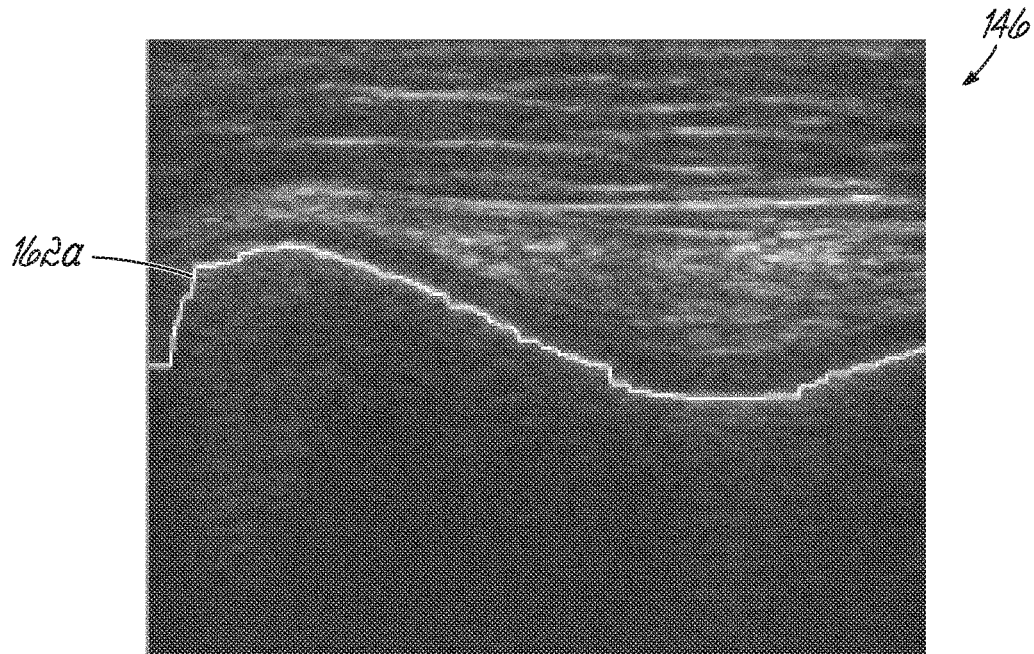
FIG. 10C is the ultrasound frame of FIG. 9B with a bone echo contour identified.
Figure 10D:
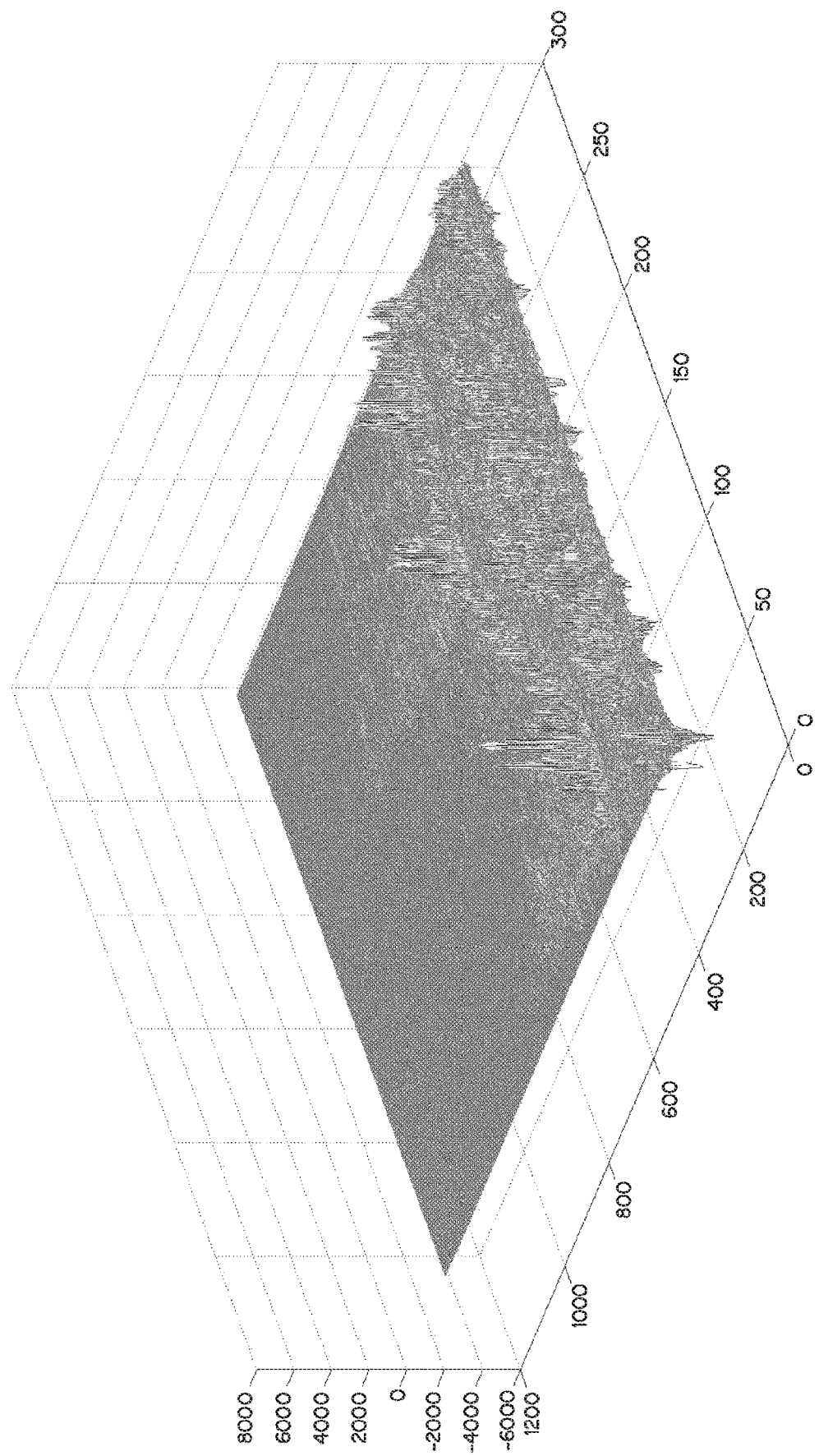
FIG. 10D is a 3-D rendering of the RF signals acquired in a data frame, which is shown in the B-mode image format in FIG. 10C.
Figure 10E:
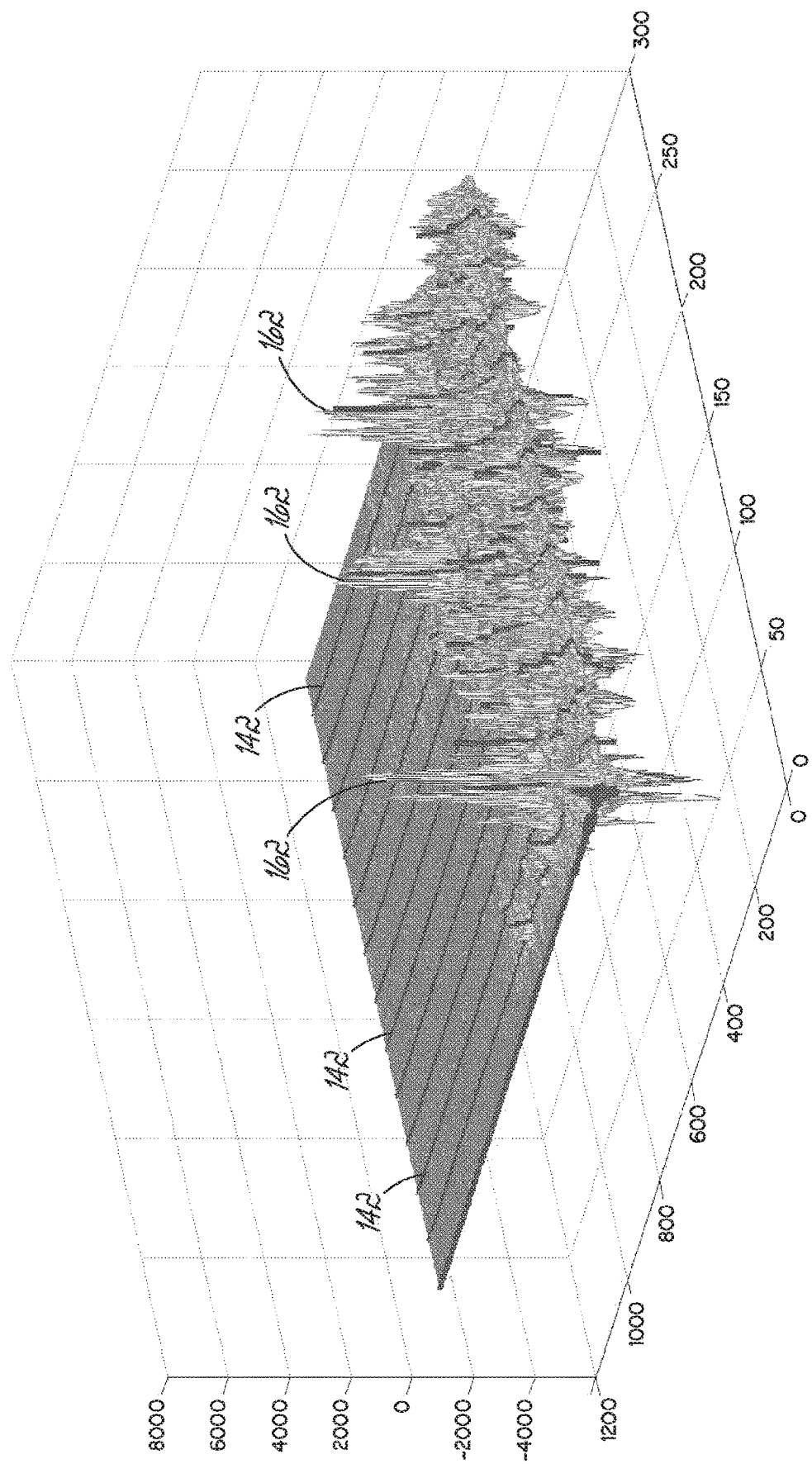
FIG. 10E is another 3-D rendering of an ultrasound frame with select ones of the RF signals delineated.

FIGS. 10B and 10C illustrate an ultrasound frame 146 having select ones of the raw RF signals 142 with some echoes 162 identified. FIGS. 10D and 10E are 3-D renderings of 2D images taken from an ultrasound frame 146 with select ones of the RF signals 142 identified in FIG. 10E.

Figure 11:
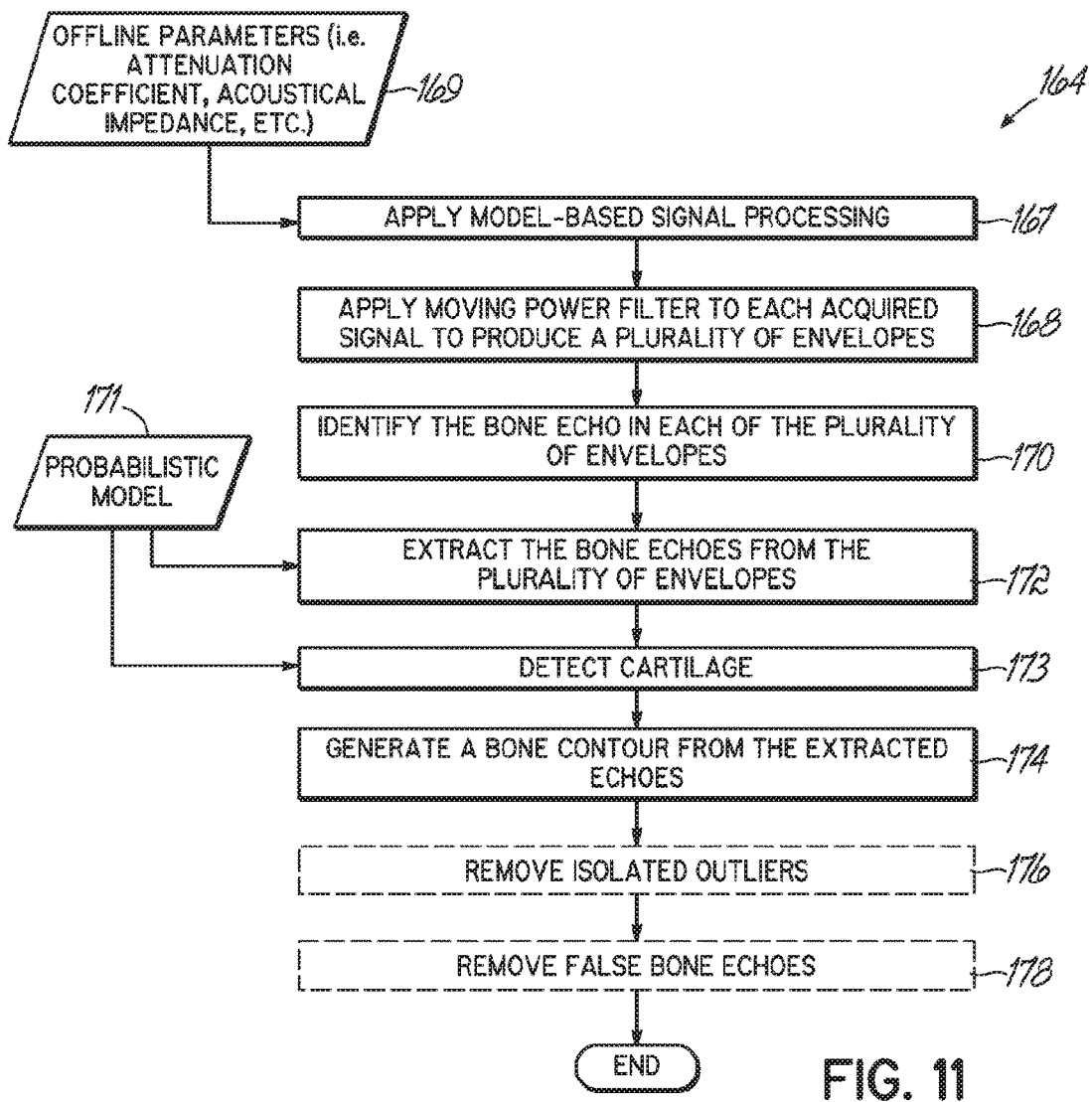
FIG. 11 is a flow chart illustrating one exemplary method of identifying and extracting the bone echo from the A-mode ultrasound RF signal.

Referring specifically now to FIG. 11, the method of extracting the bone contour 162a begins with a model-based signal processing approach incorporating a priori knowledge of an underlying physical problem into a signal processing scheme. In this way, the computer 54 (FIG. 3) may process the RF signal 142 and remove some preliminary noise based on an estimated, or anticipated, result. For example, with ultrasound signal acquisition, the physical problem is represented by the governing waveform equation, such as described in VARSLOT T, et al., "Computer Simulation of Forward Wave Propagation in Soft Tissue," *IEEE Transactions on Ultrasonics, Ferroelectrics, and Frequency Control*, 1473-1482:52(9), September 2005, the disclosure of which is incorporated herein by reference, in its entirety. The wave equation describes the propagation behavior of the ultrasonic wave in a heterogeneous medium. The solution to the wave equation may be represented as a state-space model-based processing scheme, such as described in CHEN Z, et al., "Bayesian Filtering: From Kalman Filters to Particle Filters, and Beyond," *Statistics*, 1-69, retrieved from http://citeseerx.ist.psu.edu/viewdoc/download?doi=10.1.1.107.7415&rep=rep1&type=pdf, accessed August 2011. In accordance with one embodiment of the present invention, a general solution to the model-based ultrasound wave estimator problem is developed using Bayesian estimators (e.g., maximum a posteriori), which leads to a nonlinear model-based design.

The model-based signal processing of the RF signal 142 begins with enhancing the RF signal by applying the model-based signal processing (here, the Bayesian estimator) (Block 167). To apply the Bayesian estimator, offline measurements are first collected from phantoms, cadavers, and/or simulated tissues to estimate certain unknown parameters, for example, an attenuation coefficient (i.e., absorption and scattering) and an acoustic impedance (i.e., density, porosity, compressibility), in a manner generally described in VARSLOT T (refer above), the disclosure of which is incorporated herein by reference, in its entirety. The offline measurements (Block 169) are input into the Bayesian estimator and the unknown parameters are estimated as follows:

$$z = h(x) + v \quad (6)$$

$$P(t) = e^{(-\beta t^2)} \cdot \cos(2\pi f_0 \cdot t) \quad (7)$$

Where h is the measurement function that models the system and v is the noise and modeling error. In modeling the system, the parameter, x, that best fits the measurement, z, is determined. For example, the data fitting process may find an estimate of $\hat{x}$ that best fits the measurement of z by minimizing some error norm, $\|\epsilon\|$, of the residual, where:

$$\epsilon = Z - h(x) \quad (8)$$

For ultrasound modeling, the input signal, z, is the raw RF signal from the offline measurements, the estimate $h(\hat{x})$ is based on the state space model with known parameters of the offline measurements (i.e., density, etc.). The error, v, may encompass noise, unknown parameters, and modeling errors in an effort to reduce the effect of v by minimizing the residuals and identifying the unknown parameters form repeated measurements. Weighting the last echo within a scan line by approximately 99%, as bone, is one example of using likelihood in a Bayesian framework. A Kalman filter may alternatively be used, which is a special case of the recursive Bayesian estimation, in which the signal is assumed to be linear and have a Gaussian distribution.

It would be readily appreciated that the illustrative use of the Bayesian model here is not limiting. Rather, other model-based processing algorithms or probabilistic signal processing methods may be used within the spirit of the present invention.

With the model-based signal processing complete, the RF signal 142 is then transformed into a plurality of envelopes to extract the individual echoes 162 existing in the RF signal 142. Each envelope is determined by applying a moving power filter to each RF signal 142 (Block 168) or other suitable envelope detection algorithm. The moving power filter may be comprised of a moving kernel of length that is equal to the average length of an individual ultrasound echo 162. With each iteration of the moving kernel, the power of the RF signal 142 at the instant kernel position is calculated. One exemplary kernel length may be 20 samples; however, other lengths may also be used. The value of the RF signal 142 represents the value of the signal envelope at that position of the RF signal 142. Given a discrete-time signal, X having a length, N, each envelope, Y, using a moving power filter having length, L, is defined by:

$$Y_k = \sum_{i=k-\frac{L}{2}}^{k+\frac{L}{2}} X_i^2 \ \forall \ k \in \left[ \frac{L}{2}, N - \frac{L}{2} - 1 \right] \quad (9)$$

In some embodiments, this and subsequent equations use a one-sided filter of varying length for the special cases of the samples before the L/2 sample (left-sided filter), and after the $$N - \frac{L}{2} - 1$$

sample (right-sided filter).

Each envelope produced by the moving power filter, shown in FIG. 10B, includes a plurality of local peaks (identified in FIG. 10B as enlarged dots at the intersection of each envelope with an echo 162), each being a clear representation of the individual echoes 162 existing in the acquired RF signal 142 for the various tissue interfaces. As an example of such process, FIGS. 12A-12D more clearly illustrate the RF signal 142 (top in each figure) at four iterations of the kernel of the moving power filter as well as the corresponding envelope (bottom in each figure). Individual echoes 162 in each envelope are again identified with an enlarged dot.

Of the plurality of echoes 162 in the RF signal 142, one echo 162 is of particular interest, e.g., the echo corresponding to the bone-soft tissue interface. This bone echo (hereafter referenced as 162a) is generated by the reflection of the ultrasound energy at the surface of the scanned bone. More particularly, the soft tissue-bone interface is characterized by a high reflection coefficient of 43%, which means that 43% of the ultrasound energy reaching the surface of the bone is reflected back to the transducer array 68 (FIG. 2) of the ultrasound probe 60 (FIG. 2). This high reflectivity gives bone the characteristic hyper-echoic appearance in an ultrasound image.

Bone is also characterized by a high attenuation coefficient of the applied RF signal (6.9 db/cm/mHz for trabecular bone and 9.94 db/cm/mHz for cortical bone). At high frequencies, such as those used in musculoskeletal imaging (that is, in the range of 7-14 MHz), the attenuation of bone becomes very high and the ultrasound energy ends at the surface of the bone. Therefore, an echo 162a corresponding to the soft-tissue-bone interface is the last echo 162a in the RF signal 142. The bone echo 162a is identified by selecting the last echo having a normalized envelope amplitude (with respect to a maximum value existing in the envelope) above a preset threshold (Block 170).

The bone echoes 162a are then extracted from each frame 146 (Block 172) and used to generate the bone contour existing in that RF signal 142 and as shown in FIG. 10C (Block 174). In extracting the bone echoes, a probabilistic model (Block 171) may be input and applied to the RF signals 142 of each frame 146. The probabilistic model (Block 171) may further be used in detecting cartilage within the envelopes of the RF signals 142 (Block 173). While the probabilistic signal processing method may include the Bayesian estimator described previously, in still other embodiments, the signal processing may be, a maximum likelihood ratio, neural network, or a support vector machine ("SVM"), for example, with the latter of which is further described below.

Prior to implementing the SVM, the SVM may be trained to detect cartilage in RF signals. One such way of training the SVM includes information acquired from a database comprising of MRI images and/or RF ultrasound images to train the SVM to distinguish between echoes associated with cartilage from the RF signals 142, and from within the noise or in ambiguous soft tissue echoes. In constructing the database in accordance with one embodiment, knee joints from multiple patient's are imaged using both MRI and ultrasound. A volumetric MRI image of each knee joint is reconstructed, processed, and the cartilage and the bone tissues are identified and segmented. The segmented volumetric MRI image is then registered with a corresponding segmented ultrasound image (wherein bone tissue is identified). The registration provides a transformation matrix that may then be used to register the raw RF signals 142 with a reconstructed MRI surface model.

After the raw RF signals 142 are registered with the reconstructed MRI surface model, spatial information from the volumetric MRI images with respect to the cartilage tissue may be used to determine the location of a cartilage interface on the raw RF signal 142 over the articulating surfaces of the knee joint.

The database of all knee joint image pairs (MRI and ultrasound) is then used to train the SVM. Generally, the training includes loading all raw RF signals, as well as the location of the bone-cartilage interface of each respective RF signal. The SVM may then determine the location of the cartilage interface in an unknown, input raw RF signal. If desired, a user may chose from one or more kernels to maximize a classification rate of the SVM.

In use, the trained SVM receives a reconstructed knee joint image of a new patient as well as the raw RF signals. The SVM returns the cartilage location on the RF signal data, which may be used, along with the tracking information from the tracking system (i.e., the optical markers 86 and the position sensor 88 (FIGS. 2-2A) are provided herein) to generate 3-D coordinates for each point on the cartilage interface. The 3-D coordinates may be triangulated and interpolated to form a complete cartilage surface.

Referring still to FIG. 11, the resultant bone contours may be noisy and require filtering to remove echoes 162 that may be falsely detected as the bone echo 162a. Falsely detected echoes 162 may originate from one of at least two sources: (1) an isolated outlier echoes and (2) a false bone echoes. Furthermore, some images may not include a bone echo 162a; therefore any detected echo 162 is noise and should be filtered out. Therefore, proper determination of the preset threshold or filtering algorithm may prevent the false selection of a falsely detected echo 162.

Isolated outliers are those echoes 162 in the RF signal 142 that correspond to a tissue interface that is not the soft-tissue-bone interface. Selection of the isolated outliers may occur when the criterion is set too high. If necessary, the isolated outliers may be removed (Block 176) by applying a median filter to the bone contour. That is, given a particular bone contour, X having a length, N, with a median filter length, L, the median-filter contour, $Y_k$, is:

$$Y_k = \text{Median}\left[X_{k-\frac{L}{2}}, X_{k+\frac{L}{2}}\right] \forall k \in \left[\frac{L}{2}, N - \frac{L}{2} - 1\right] \quad (10)$$

False bone echoes are those echoes 162 resulting from noise or a scattering echo, which result in a detected bone contour in a position where no bone contour exists. The false bone echoes may occur when an area that does not contain a bone is scanned, the ultrasound probe 60 (FIG. 2) is not oriented substantially perpendicular with respect to the bone surface, the bone lies deeper than a selected scanning depth, the bone lies within the selected scanning depth but its echo is highly attenuated by the soft tissue overlying the bone, or a combination of the same. Selection of the false bone echoes may occur when the preset threshold is too low.

Frames 146 containing false bone echoes should be removed. One such method of removing the false bone echoes (Block 178) may include applying a continuity criteria. That is, because the surface of the bone has a regular shape, the bone contour, in the two-dimensions of the ultrasound image, should be continuous and smooth. A false bone echo will create a non-continuity, and exhibits a high degree of irregularity with respect to the bone contour.

One manner of filtering out false bone echoes is to apply a moving standard deviation filter; however, other filtering methods may also be used. For example, given the bone contour, X having a length, N, with a median filter length, L, the standard deviation filter contour:

$$Y_k = \sqrt{\frac{1}{L-1} \sum_{i=k-\frac{L}{2}}^{i=k-\frac{L}{2}} (X_i - \overline{X})^2} \ \forall k \in \left[\frac{L}{2}, N - \frac{L}{2} - 1\right] \quad (11)$$

Where $Y_k$ is the local standard deviation of the bone contour, which is a measure of the regularity and continuity of the bone contour. Segments of the bone contour including a false bone echo are characterized by a higher degree of irregularity and have a high $Y_k$ value. On the other hand, segments of the bone contour including only echoes resulting from the surface of the bone are characterized by high degree regularity and have a low $Y_k$ value.

A resultant bone contour 180, resulting from applying the moving median filter and the moving standard deviation filter, includes a full length contour of the entire surface of the bone, one or more partial contours of the entire surface, or contains no bone contour segments.

Figure 13A:
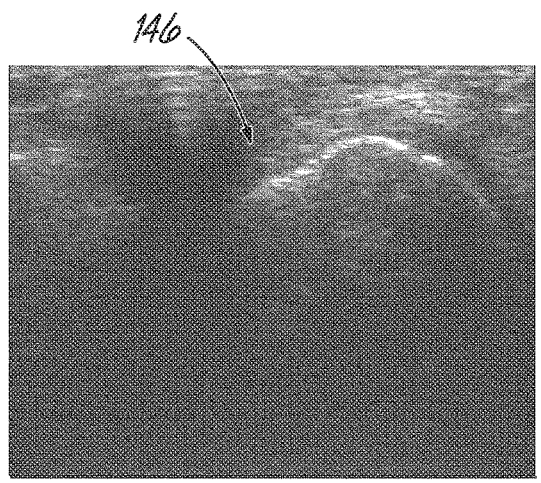
FIGS. 13A and 13D are B-mode ultrasound frames calculated from exemplary A-mode ultrasound RF signals.
Figure 13D:
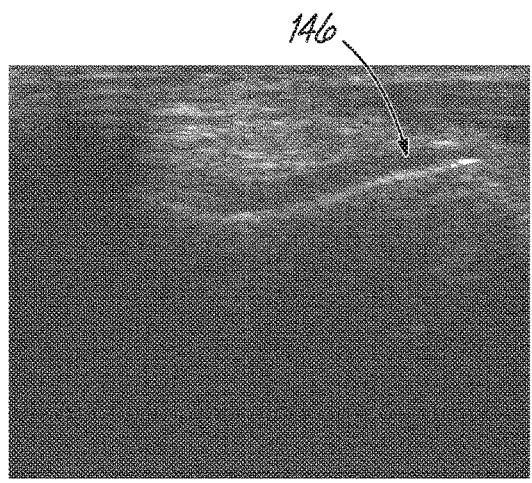
Figure 13B:
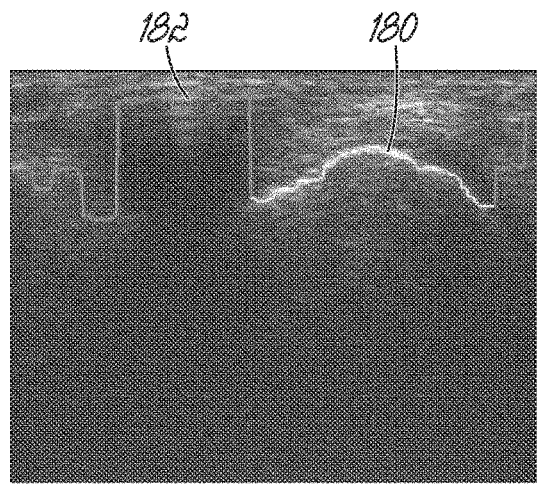
FIGS. 13B and 13E are ultrasound frames corresponding to FIGS. 13A and 13-D, respectively, with a bone contour identified before noise removal and overlain on the B-mode image.
Figure 13E:
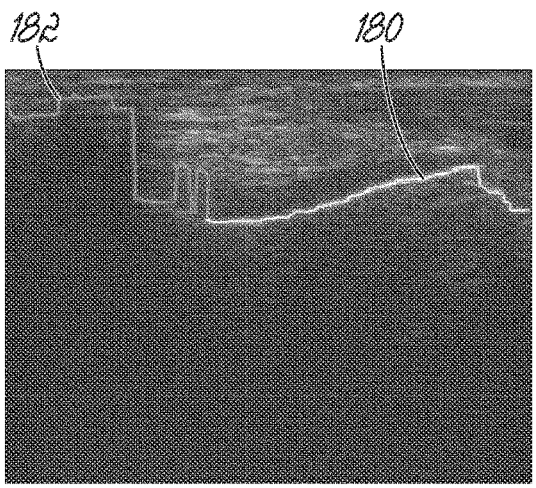
Figure 13C:
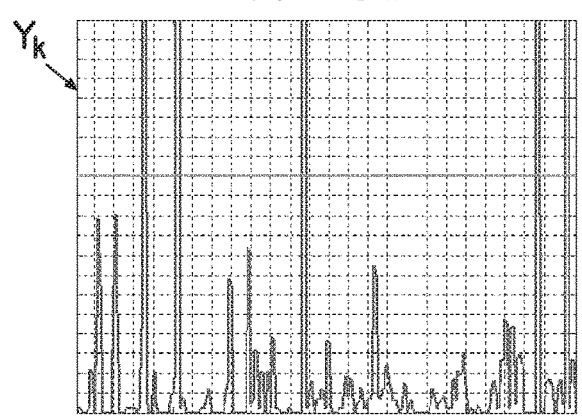
FIGS. 13C and 13F are plots of the local standard deviation of the bone contours of FIGS. 13B and 13E, respectively.
Figure 13F:
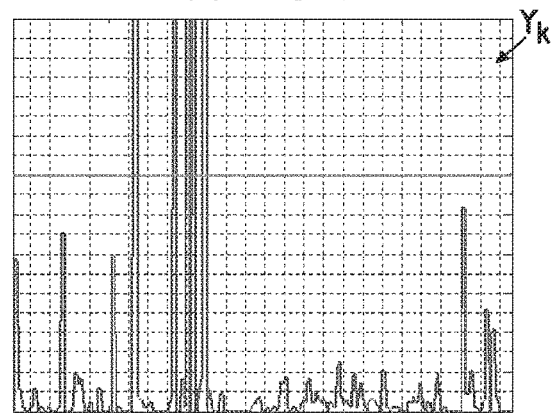
Figure 14A:
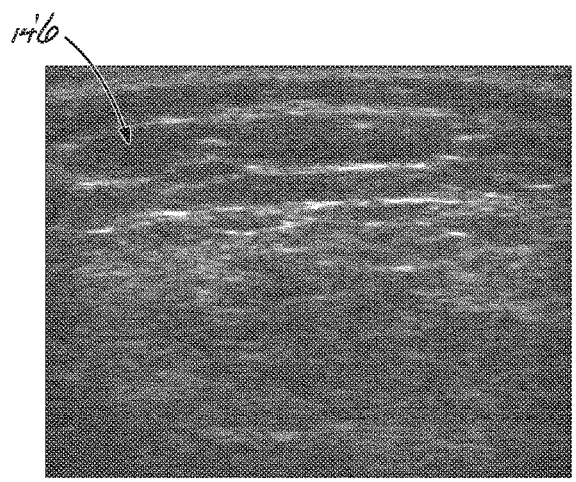
FIGS. 14A and 14D are ultrasound frames illustrating exemplary B-mode images constructed from A-mode ultrasound RF signals, and in which no bone tissue was scanned.
Figure 14D:
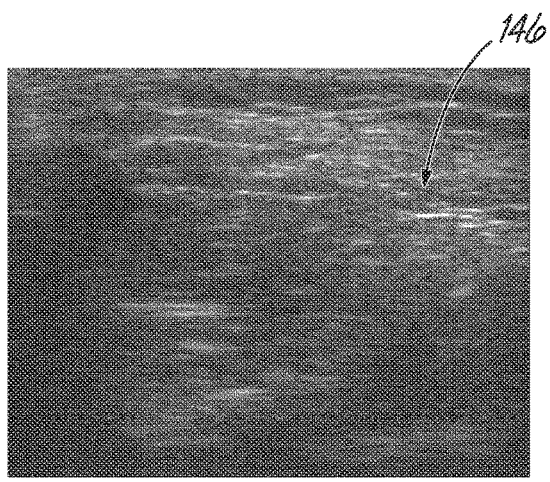
Figure 14B:
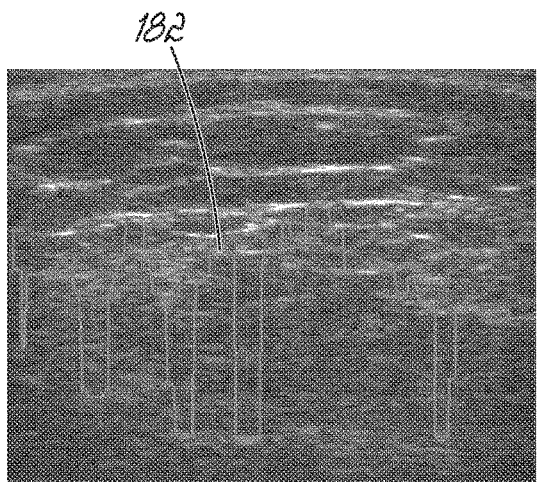
FIGS. 14B and 14E are ultrasound frames corresponding to FIGS. 14A and 14D, respectively, with the noisy false bone contours shown.
Figure 14E:
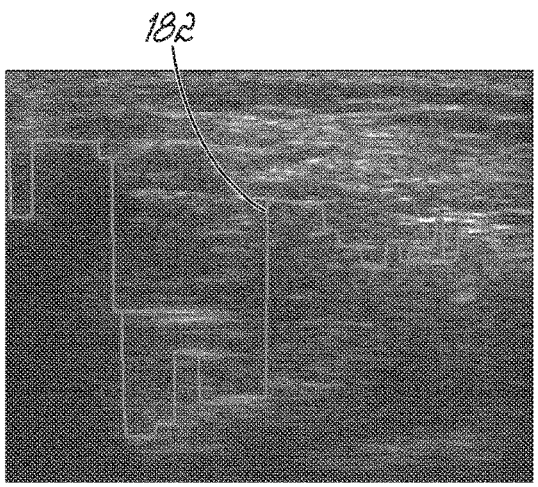
Figure 14C:
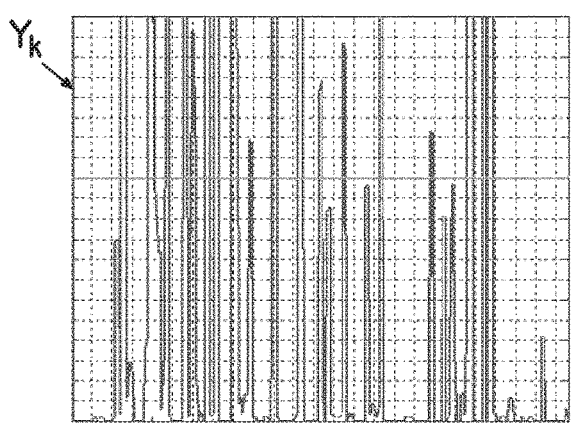
FIGS. 14C and 14F are plots of the local standard deviation of the last echoes of FIGS. 14B and 14E, respectively.
Figure 14F:
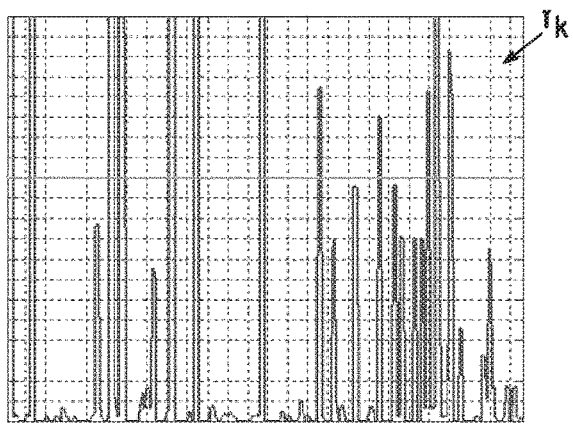

FIGS. 12A-12F and 13A-13F illustrate the resultant bone contour 180 that is selected from those segments of the extracted bone contour that satisfy two conditions: (1) the continuity criteria, having a local standard deviation value below selected standard deviation threshold and (2) a minimum-length criteria, which avoids piecewise-smooth noise contour segments from being falsely detected as bone contour. In some exemplary embodiments, the length of the standard deviation filter may be set to 3 and the threshold set to 1.16 mm, which may correspond to 30 signal samples. Accordingly, FIGS. 13A and 13D illustrate two exemplary RF signals 142 with the resultant bone contours 180 extracted and filtered from the noise 182 (including isolated outliers and false body echoes), shown in FIGS. 13B and 13E, respectively. FIGS. 13C and 13F respectively illustrate the standard deviation, $Y_k$, calculated as provided in Equation 11 above. FIGS. 14A-14F are similar to FIGS. 13A-13F, but include two exemplary signals 142 in which no bone tissue was scanned.

With the bone contours isolated from each of the RF signals, the bone contours may now be transformed into a point cloud. For instance, returning now to FIG. 7, the resultant bone contours 180 may then undergo registration with the optical system to construct a bone point cloud 194 representing the surface of at least a portion of each scanned bone (Block 186), which is described herein as a multiple step registration process. In one embodiment, the process is a two-step registration process. The registration step (Block 186) begins by transforming the resultant bone contour 180 from a 2D contour in the ultrasound frame into a 3-D contour in the world frame (Block 188). This transformation is applied to all resultant bone contours 180 extracted from all of the acquired RF signals 142.

To transform the resultant bone contour 180 into the 3-D contour, each detected bone echo 162a undergoes transformation into a 3-D point as follows:

$$d_{echo} = n_{echo} T_s C_{us} \quad (12)$$

$$l_{echo} = L_{trans} \frac{n_{line}}{N_{lines}} \hat{u}_x \quad (13)$$

$$P_{echo}^{OP} = P_{trans-origin} + d_{echo} \hat{u}_y + l_{echo} \hat{u}_x \quad (14)$$

$$P_{echo}^{W} = H_{OP}^{W} P_{echo}^{OP} \quad (15)$$

Where the variables are defined as follows:

| | |
|---|---|
| $d_{echo}$ | depth of the bone echo (cm) |
| $n_{echo}$ | sample index of the detected bone echo |
| $T_s$ | RF signal sampling period (sec/sample) |
| $C_{us}$ | speed of ultrasound in soft tissue (154 × 10³ cm/s) |
| $l_{echo}$ | distance from the $P_{trans-origin}$ (FIG. 2) of the transducer array 68 (FIG. 2) to the current scan line (cm) |
| $P_{echo}^{OP}$ | detected point on the bone surface represented in the local frame |
| $n_{line}$ | index of the scan line containing the bone echo in the image |
| $N_{lines}$ | number of scan lines in the image |
| $P_{echo}^{W}$ | detected surface of the bone relative to the world frame |
| $H_{OP}^{W}$ | homogeneous transformation between the local frame and the world frame, as described previously |
| $H_{OP}^{W}$ | dynamically obtained transformation that contains the position and orientation of the optical marker 86 (FIG. 2) |

If so desired, an intermediate registration process may be performed between the resultant bone contour and a B-mode image, if acquired (Block 190). This registration step is performed for visualizing the resultant bone contour 180 with the B-mode image (FIG. 9), which provides visual validation and feedback of the resultant bone contour 180 detection process, in real time, while the user is performing the scan. This visual validation may aid the user in determining whether acquisition is completed (Block 160), as described previously. More specifically, the resultant bone contour 180 is registered with the B-mode image by:

$$P_{echo}^{I} = (l_{echo} I_x, d_{echo} I_y) \quad (16)$$

Where $I_x$ and $I_y$ denote the B-mode image resolution (pixels/cm) for the x- and y-axes respectively. $P_{echo}^{I}$ denotes the coordinates of the bone contour point relative to the ultrasound frame.

Figure 15:
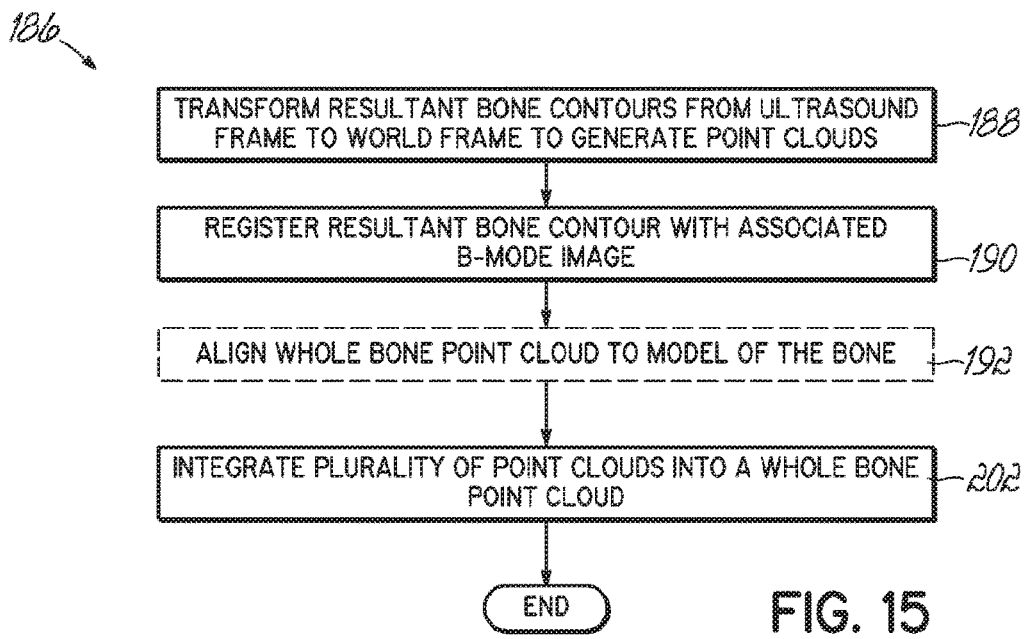
FIG. 15 is a flow chart illustrating one exemplary method of generating a bone point cloud from the isolated bone contours.
Figure 12A:
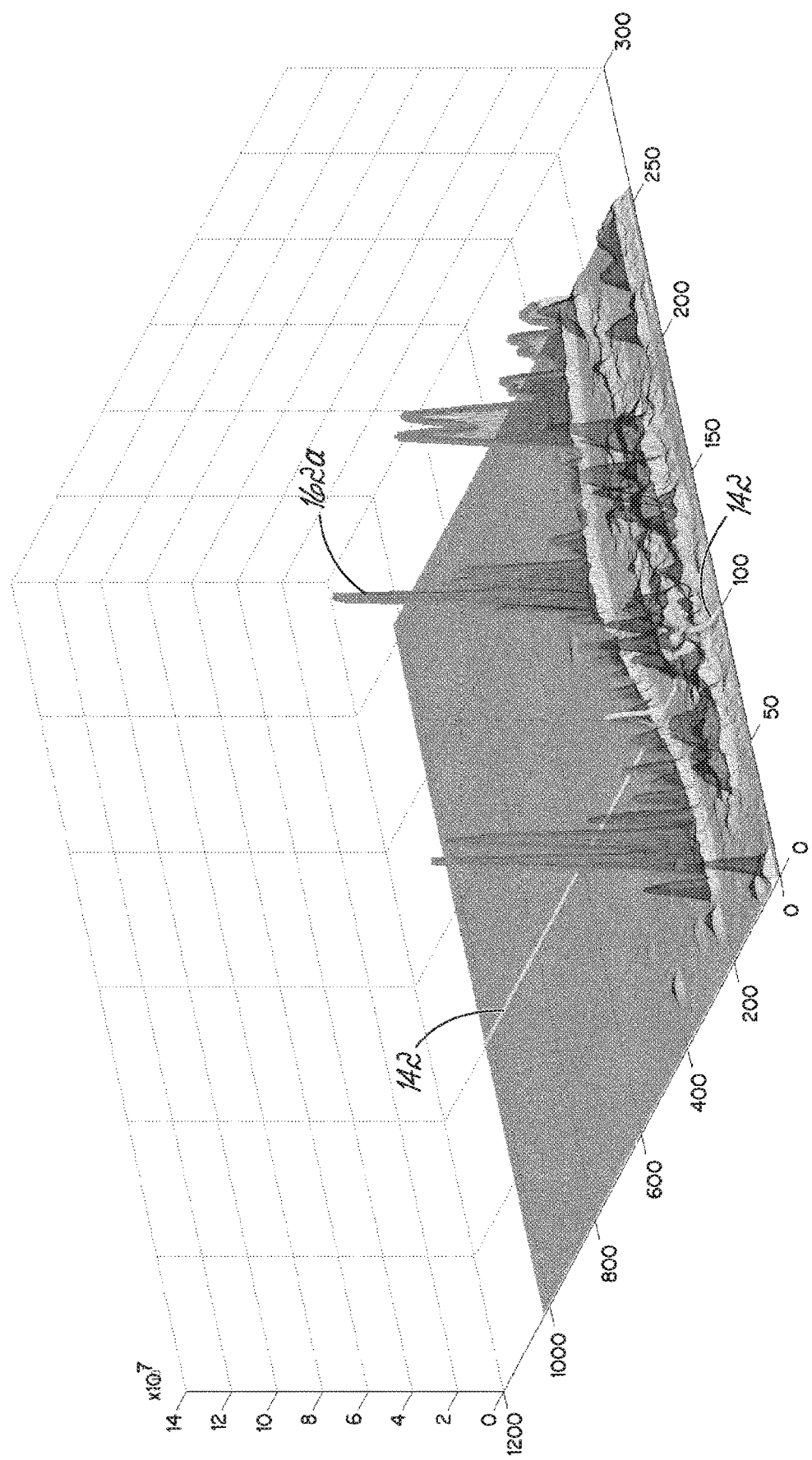
FIG. 12A is a 3-D rendering of an ultrasound frame after envelope detection.
Figure 12B:
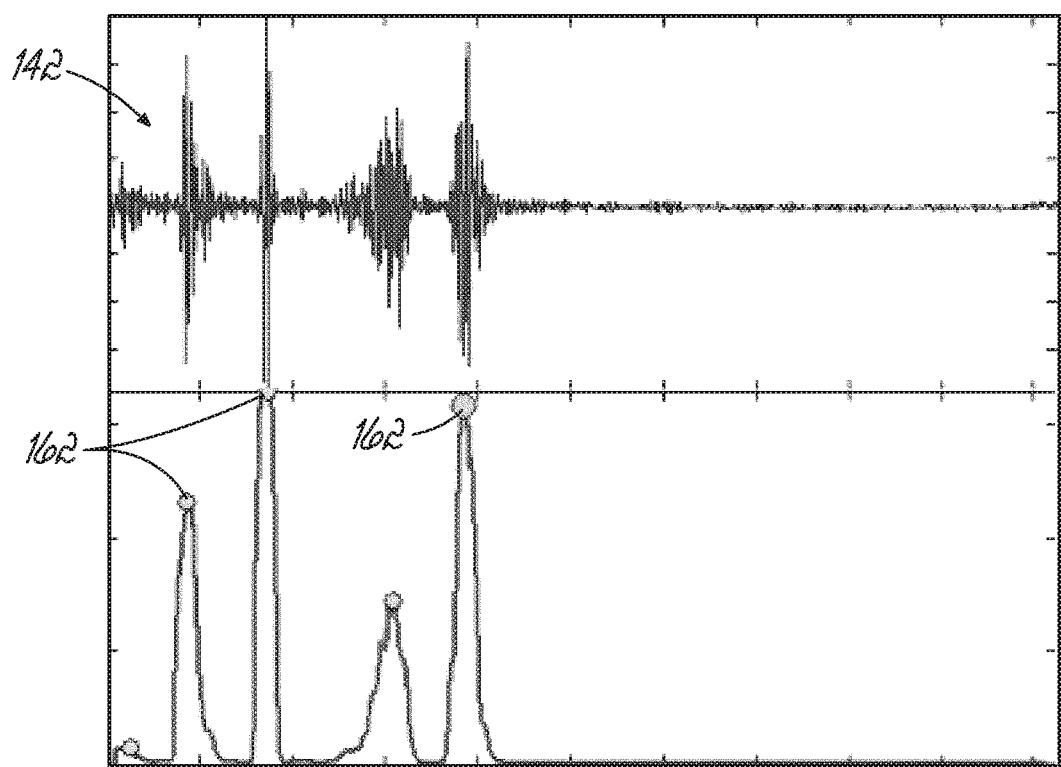
FIGS. 12B-12E respectively illustrate four exemplary envelopes of the sampled A-mode ultrasound RF signal, with the echoes identified in each envelope.
Figure 12C:
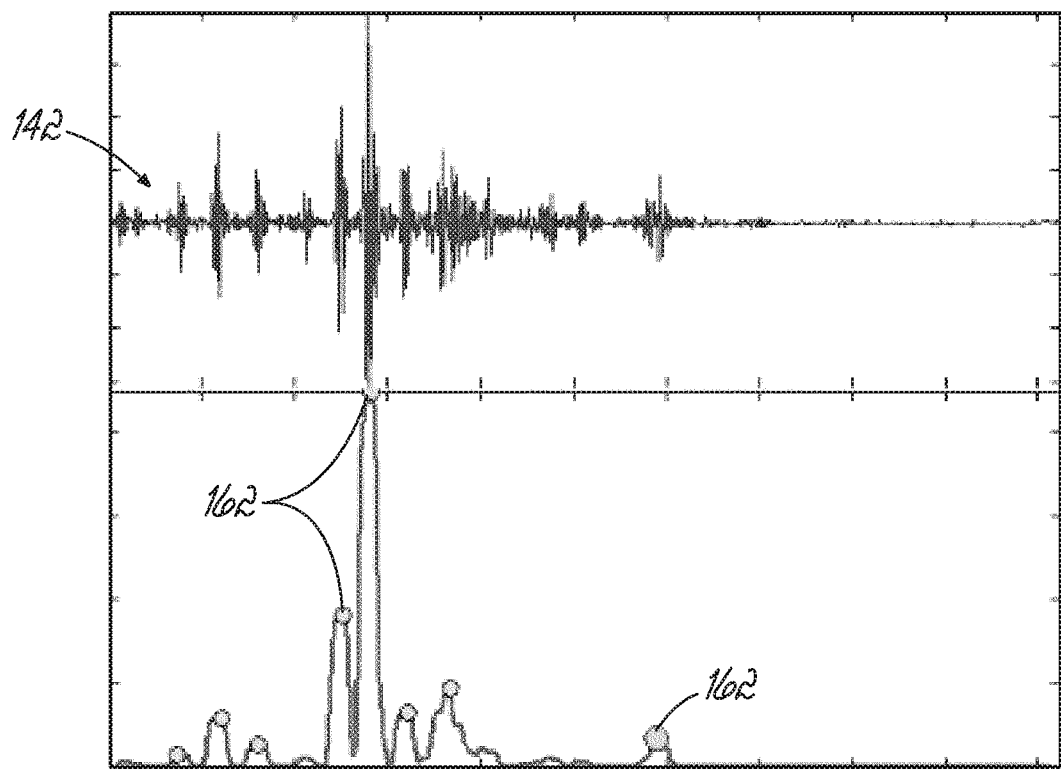
Figure 12D:
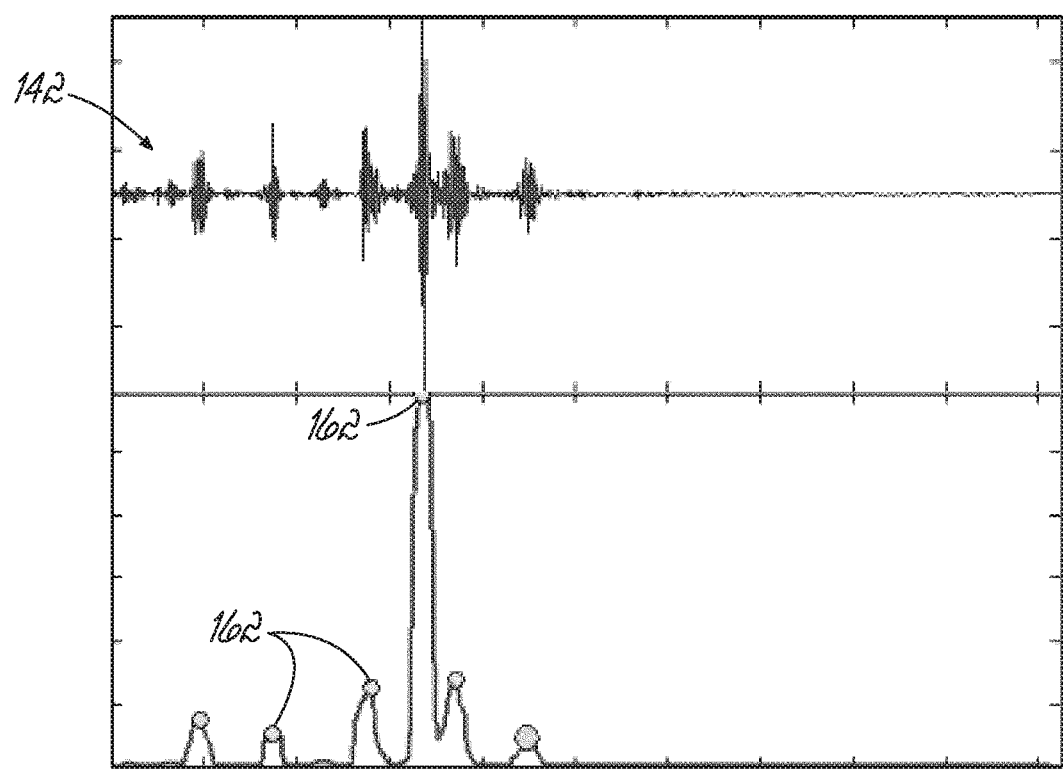
Figure 12E:
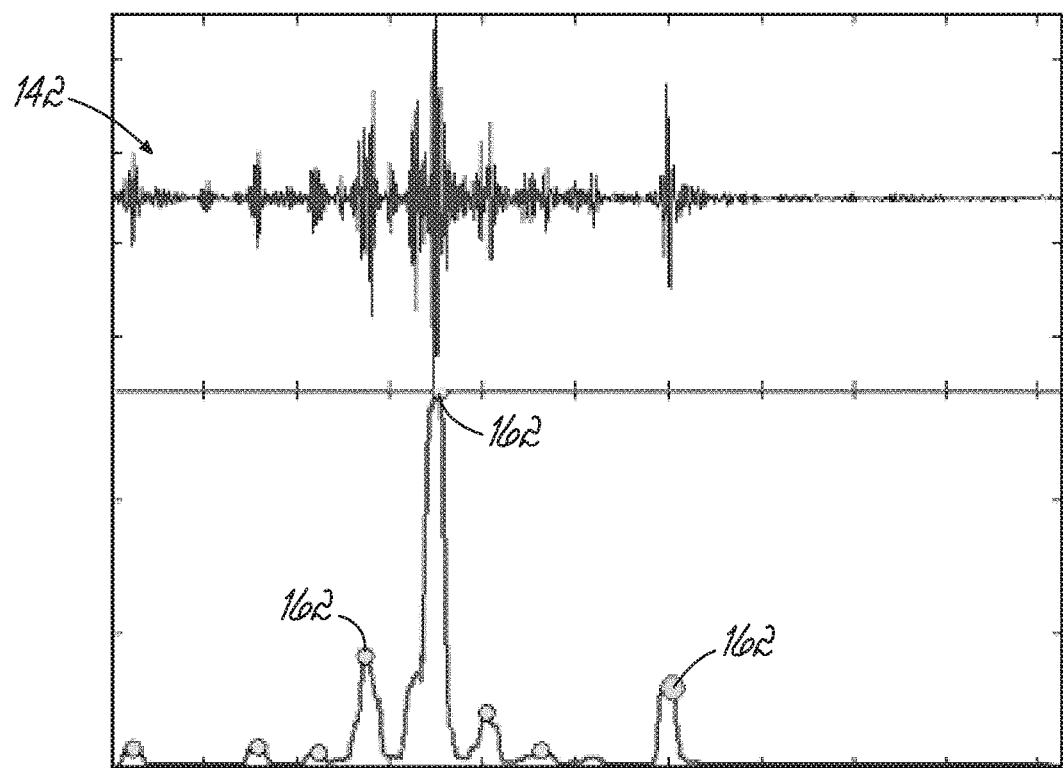

After the resultant bone contours 180 are transformed and, if desired, registered (Block 190) (FIG. 15), the plurality of point clouds 165 (FIG. 16B) are generated representing the surface of the bone. During the second registration process the plurality of point clouds 165 are integrated into a bone point cloud 194 representing the entire surface of the scanned bone.

To begin the second registration process, as shown in FIGS. 16A-17D, the plurality of point clouds 164 are initially aligned to a standardized model of the scanned bone, here a model femur 200, for example, by using 4-6 previously specified landmarks 196 (Block 192). More specifically, the user may identify the plurality of landmarks 196 on the model femur 200, which need not be identified with high accuracy. After this initial alignment, an iterative closest point ("ICP") alignment is performed to more accurately align the plurality of point clouds to the standardized model. If necessary, noise may be removed by thresholding for a distance between a respective point of the plurality of point clouds and the closest vertices in the model femur 200; however, other filtering methods may alternatively be used. For instance, an average distance plus one standard deviation may be used as the threshold. The process is repeated for each point cloud 165 of the plurality for the surface of the scanned bone.

The now aligned point clouds 165 are then integrated into a single uniform point cloud 194 that represents the surface of the scanned bone (Block 202).

Figure 18:
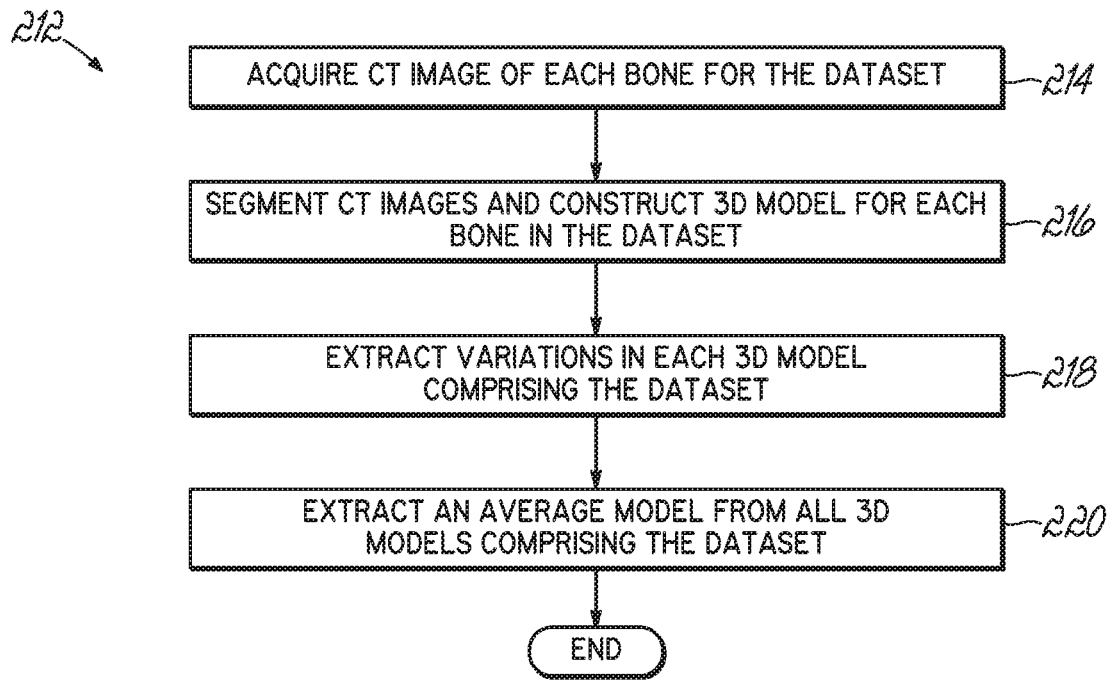
FIG. 18 is a flow chart illustrating one exemplary method of generating a statistical atlas of bone models.

After the point clouds 194 are formed, a bone model may be optimized in accordance with the point clouds 194. That is, the bone point cloud 194 is then used to reconstruct a 3-D patient-specific model of the surface of the scanned bone. The reconstruction begins with a determination of a bone model from which the 3-D patient-specific model is derived (Block 210). The bone model may be a generalized model based on multiple patient bone models and may be selected from a principle component analysis ("PCA") based statistical bone atlas. One such a priori bone atlas, formed in accordance with the method 212 of FIG. 18, includes a dataset of 400 dry femur and tibia bone pairs, scanned by CT (Block 214) and segmented to create models of each bone (Block 216). The method of building and using one such statistical atlas is described in MAHFOUZ M et al., "Automatic Methods for Characterization of Sexual Dimorphism of Adult Femora: Distal Femur," *Computer Methods in Biomechanics and Biomedical Engineering*, 10(6) 2007, the disclosure of which is incorporated herein by reference in its entirety.

Each bone model, $M_i$, (where $I \in [1, N]$, N being the number of models in the dataset) has the same number of vertices, wherein the vertex, $V_j$ in a select one model corresponds (at the same anatomical location on the bone) to the vertex, $V_j$ in another one model within the statistical atlas.

PCA was then performed on each model in the dataset to extract the modes of variation of the surface of the bone (Block 218). Each mode of variation is represented by a plurality of eigenvectors resulting from the PCA. The eigenvectors, sometimes called eigenbones, define a vector space of bone morphology variations extracted from the dataset. The PCA may include any one model from the dataset, expressed as a linear combination of the eigenbones. An average model of all of the 3-D models comprising the dataset is extracted (Block 220) and may be defined as:

$$M_{avg} = \frac{1}{N} \sum_{i=1}^{N} M_i \quad (17)$$

$$M_i = M_{avg} + \Sigma_{k=1}^{L} \alpha_{ik} U_k \quad \forall i \in [1, N] \quad (18)$$

Where the variables are defined as follows:

| | |
|---|---|
| $M_{avg}$ | is the mean bone of the dataset |
| L | dimensionality of the eigenspace (i.e., the number of eigenbones) and is equal to N |
| N | number of models in the data |

-continued

| | |
|---|---|
| $U_k$ | $k^{th}$ eigenbone |
| $\alpha_{ik}$ | $k^{th}$ shape descriptor or eigenbone's coefficient for the $i^{th}$ model |

Furthermore, any new model, $M_{new}$, i.e., a model not already existing in the dataset, may be approximately represented by new values of the shape descriptors (eigenvectors coefficients) as follows:

$$M_{new} \cong M_{avg} + \Sigma_{k=1}^{W} \alpha_k U_k \qquad (19)$$

Where the variables are defined as follows:

| | |
|---|---|
| $M_{new}$ | new bone model |
| $\alpha_k$ | indexed shape descriptors for the new model |
| W | number of principal components to use in the model approximation, where $W \leq L$ |

The accuracy of $M_{new}$ is directly proportional to the number of principal components (W) used in approximating the new model and the number of models, L, of the dataset used for the PCA. The residual error or root mean square error ("RMS") for using the PCA shape descriptors is defined by:

$$RMS = rms[M_{new} - (M_{avg} + \Sigma_{k=1}^{W} \alpha_k U_k)] \qquad (20)$$

Therefore, the RMS when comparing any two different models, A and B, having the same number of vertices is defined by:

$$RMS = rms(A - B) = \sqrt{\frac{\sum_{j=1}^{m} \|V_{Aj} - V_{Bj}\|^2}{m}} \qquad (21)$$

Where $V_{Aj}$ is the $j^{th}$ vertex in model A, and similarly, $V_{Bj}$ is the $j^{th}$ vertex in model B.

Returning again to FIG. 7, the average model ("AVERAGE" branch of Block 210) is loaded (Block 230) or a subset model is selected ("SELECTED" branch of Block 210) from the statistical atlas based on demographics that are similar to the patient and loaded (Block 232) for optimization. The bone point cloud 194 is then applied to the loaded model (Block 234) so that the shape descriptors of the loaded model may be changed to create the 3-D patient-specific model. If desired, one or more shape descriptors may be constrained ("YES" branch of Block 254) so that the 3-D patient-specific model will have the same anatomical characteristics as the loaded model. Accordingly, the one or more shape descriptors are set (Block 238). With the constraints set, the loaded model may be deformed (or optimized) (Block 240) into a model that resembles the appropriate bone and not an irregularly, randomly shaped model. If no constraints are desired ("NO" branch of Block 240) and then the loaded model is optimized (Block 240).

Changing the shape descriptors to optimize the loaded model (Block 240) may be carried out by one or more optimization algorithms, guided by a scoring function, to find the values of the principal components coefficients to create the 3-D patient-specific new model and are described with reference to FIG. 19. The illustrated optimization algorithm includes a two-step optimization method of successively-applied algorithms to obtain the 3-D patient-specific model that best fits the bone point cloud 194 as discussed below. Although a two-step method is described, the present invention is not limited to just a two-step optimization method.

The first algorithm may use a numerical method of searching the eigenspace for optimal shape descriptors. More specifically, the first algorithm may be an iterative method that searches the shape descriptors of the loaded model to find a point that best matches the bone point cloud 194 (Block 250). One such iterative method may include, for example, Powell's conjugate gradient descent method with a RMS as the scoring function. The changes are applied to the shape descriptors of the loaded model by the first algorithm to form a new model, $M_{new}$, (Block 252) defined by Equation 19. The new model, $M_{new}$, is then compared with the bone point cloud 194 and the residual error, E, calculated to determine whether a further iterative search is required (Block 254). More specifically, given a bone point cloud, Q, having n points therein, and an average model, $M_{avg}$, with I vertices, there may be a set of closest vertices, V in the average model, $M_{avg}$ to the bone point cloud, Q.

$$v_i = \text{argmin}_{v_j \in M} \|v_j - q_i\| \forall i \in [1,n], j \in [1,I] \qquad (22)$$

Where $v_i$ is the closest point in the set, V, to $q_i$ in the bone point cloud, Q. An octreemay be used to efficiently search for the closest points in $M_{new}$. The residual error, E, between the new model, $M_{new}$ and the bone point cloud, Q, is then defined as:

$$E = \|V - Q\|^2 \qquad (23)$$

With sufficiently high residual error ("YES" branch of Block 254), the method returns to further search the shape descriptors (Block 250). If the residual error is low ("NO" branch of Block 254), then the method proceeds.

The second algorithm of the two-step method refines the new model derived from the first algorithm by transforming the new model into a linear system of equations in the shape descriptors. The linear system is easily solved by linear system equation, implementing conventional solving techniques, which provide the 3-D patient-specific shape descriptors.

Figure 19:
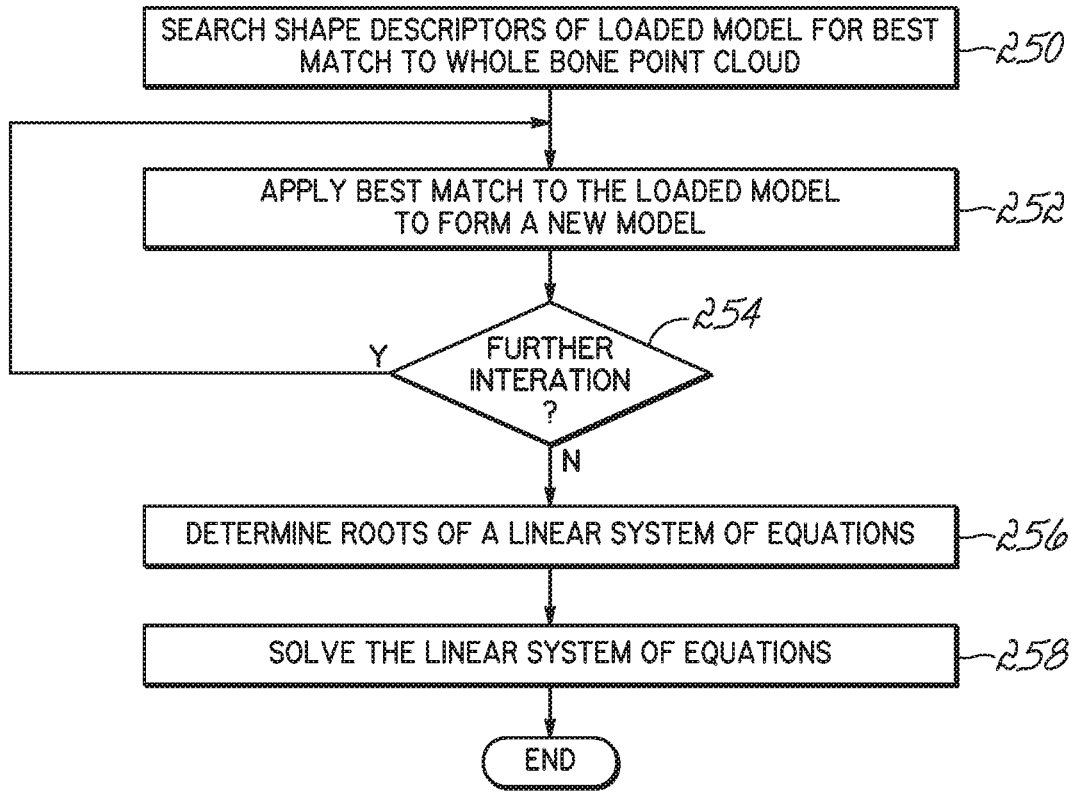
FIG. 19 is a flow chart illustrating one exemplary method of optimizing a bone model to the bone point cloud.

In continuing with FIG. 19, and to transform the new model into the linear system, the roots of the linear system must be determined (Block 256). More specifically, the first partial derivatives of the residual error, E, with respect to the shape descriptors, $\alpha_k$, are equal to zero. The error function, Equation 23, may be expressed in terms of the vertices, $v_i$, of the set, V, and the points, $p_i$, of the point cloud, Q:

$$E = \Sigma_{i=1}^{m} \|v_i - q_i\|^2 \qquad (24)$$

And may also be expressed in terms of the new model's shape descriptors as:

$$E = \|(V_{avg} + \Sigma_{k=1}^{W} \alpha_k U'_k) - Q\|^2 \qquad (25)$$

Where $V_{avg}$ is the set of vertices from the loaded model's vertices, which corresponds to the vertices set, V, that contains the closest vertices in the new model, $M_{new}$, that is being morphed to fit the bone point cloud, Q. $U'_k$ is a reduced version of the $k^{th}$ eigenbone, $U_k$, containing only the set of vertices corresponding to the vertices set, V.

Combining Equations 24 and 25, E maybe expressed as:

$$E = \Sigma_{i=1}^{m} \|(v_{avg,i} + \Sigma_{k=1}^{W} \alpha_k u'_{k,i}) - q_i\|^2 \qquad (26)$$

Where $v_{avg,i}$ is the $i^{th}$ vertex of $V_{avg}$. Similarly, $u'_{k,i}$ is the $i^{th}$ vertex of the reduced eigenbone, $U'_k$.

The error function may be expanded as:

$$E = \Sigma_{i=1}^{m} [(x_{avg,i} + \Sigma_{l=1}^{W} \alpha_k x_{u',l,i} - x_{q,i})^2 + (y_{avg,i} + \Sigma_{l=1}^{W} \alpha_k y_{u',l,i} - y_{q,i})^2 + (z_{avg,i} + \Sigma_{l=1}^{W} \alpha_k z_{u',l,i} - z_{q,i})^2] \qquad (27)$$

Where $x_{avg,i}$ is the x-coordinate of the $i^{th}$ vertex of the average model, $x_{k,i}$ is the x-coordinate of the $i^{th}$ vertex of the $k^{th}$ eigenbone, and $x_{Q,i}$ is the x-coordinate of the $i^{th}$ point of the point cloud, Q. Similar arguments are applied to the y- and z-coordinates. Calculating the partial derivative of E with respect to each shape descriptor, $\alpha_k$, yields:

$$\frac{\partial E}{\partial \alpha_k} = 0 \ \forall \ k \in [1, W] \tag{28}$$

$$\frac{\partial E}{\partial \alpha_k} = \sum_{i=1}^{m}\left[2\left(x_{avg,i} + \sum_{l=1}^{W} a_l x_{u',l,i} - x_{p,i}\right)x_{k,i} + 2\left(y_{avg,i} + \sum_{l=1}^{W} a_l y_{u',l,i} - y_{p,i}\right)y_{k,i} + 2\left(z_{avg,i} + \sum_{l=1}^{W} a_k z_{u',l,i} - z_{p,i}\right)z_{k,i}\right] = 0 \ \forall \ k \in [1, W] \tag{29}$$

Recombining the coordinate values into vectors yields:

$$\frac{\partial E}{\partial \alpha_k} = \sum_{i=1}^{m}\left[(v_{avg,i} \cdot u'_{k,i}) + \left(\sum_{l=1}^{W} a_l u'_{l,i}\right) \cdot u'_{k,i} - q_i \cdot u'_{k,i}\right] = 0 \ \forall \ k \in [1, W] \tag{30}$$

And with rearrangement:

$$\Sigma_{i=1}^{m}(\Sigma_{l=1}^{w} a_l (u'_{l,i} \cdot u'_{k,i})) = \Sigma_{i=1}^{m}[q_i \cdot u'_{k,i} - (v_{avg,i} \cdot u'_{k,i})] \tag{31}$$

Reformulating Equation 31 into a matrix form provides a linear system of equations in the form of Ax=B:

$$\sum_{i=1}^{m} \begin{bmatrix} u'_{1,i} \cdot u'_{1,i} & u'_{2,i} \cdot u'_{1,i} & \cdots & \cdots & u'_{W,i} \cdot u'_{1,i} \\ u'_{1,i} \cdot u'_{2,i} & u'_{2,i} \cdot u'_{2,i} & \cdots & \cdots & u'_{W,i} \cdot u'_{2,i} \\ \vdots & \vdots & \ddots & \ddots & \vdots \\ \vdots & \vdots & \ddots & \ddots & \vdots \\ u'_{1,i} \cdot u'_{W,i} & u'_{2,i} \cdot u'_{W,i} & \cdots & \cdots & u'_{W,i} \cdot u'_{W,i} \end{bmatrix} \begin{bmatrix} a_1 \\ a_2 \\ \vdots \\ \vdots \\ a_W \end{bmatrix} = \sum_{i=1}^{m} \begin{bmatrix} (q_i - v_{avg,i}) \cdot u'_{1,i} \\ (q_i - v_{avg,i}) \cdot u'_{2,i} \\ \vdots \\ \vdots \\ (q_i - v_{avg,i}) \cdot u'_{W,i} \end{bmatrix} \tag{32}$$

The linear system of equations may be solved using any number of known methods, for instance, singular value decomposition (Block 258).

In one embodiment, the mahalanobis distance is omitted because the bone point clouds are dense, thus providing a constraining force on the model deformation. Therefore the constraining function of the mahalanobis distance may not be needed, but rather was avoided to provide the model deformation with more freedom to generate a new model that best fit the bone point cloud.

An ultrasound procedure in accordance with the embodiments of the present invention may, for example, generate approximately 5000 ultrasound images. The generated 3-D patient-specific models (Block 260, FIG. 7), when compared against CT-based segmented models, yielded an average error of approximately 2 mm.

The solution to the linear set of equations provides a description of the patient-specific 3-D model, derived from an average, or select model, from the statistical atlas, and optimized in accordance with the point cloud transformed from a bone contour that was isolated from a plurality of RF signals. The solution may be applied to the average model to display a patient-specific 3-D bone model for aiding in pre-operative planning, mapping out injection points, planning a physical therapy regiment, or other diagnostic and/or treatment-based procedure that involves a portion of the musculoskeletal system.

Cartilage 3-D models may be reconstructed a method that is similar to that which was outlined above for bone. During contour extraction, the contour of the cartilage is more difficult to detect than bone. Probabilistic modeling (Block 171) is used to process the raw RF signal to more easily identify cartilage, and SVM aids in detection of cartilage boundaries (Block 173) based on MRI training sets. A cartilage statistical atlas is formed by a method that may be similar to what was described for bone; however, as indicated previously, MRI is used rather than the CT (which was the case for bone). The segmentation (Block 216), variation extraction (Block 218) and base model morphing (Block 240) (FIG. 19) are processed to produce a reconstructed cartilage model in the same manner as a bone model is reconstructed. The cartilage model may be displayed alone, or in conjunction with the 3D patient-specific bone model.

While the present invention has been illustrated by the description of the embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the present invention in its broader aspects is not limited to the specific details representative apparatus and method, and illustrative examples shown and described. Accordingly, departures may be made from such details without departure from the spirit or scope of applicant's general inventive concept.

What is claimed is:

1. A method of generating a virtual three dimensional subject-specific musculoskeletal model, the method comprising:
   generating an envelope for each of a plurality of raw signals obtained from an ultrasound scan of at least a portion of a subject, each envelope including one or more peaks;
   generating contour lines based on the peaks of the envelopes;
   transforming the contour lines into a three dimensional (3-D) point cloud using tracking information obtained by tracking a position of an ultrasound transducer during the ultrasound scan of at least the portion of the subject; and optimizing a template tissue model with respect to the point cloud to generate a virtual three dimensional subject-specific musculoskeletal model.

2. The method according to claim 1, wherein the plurality of raw signals includes a first raw signal at a first frequency and a second raw signal at a second frequency, where the first frequency is different than the second frequency.

3. The method according to claim 1, further comprising:
transmitting ultrasound signals during the ultrasound scan; and
obtaining the plurality of raw signals responsive to transmitting the ultrasound signals.

4. The method according to claim 3, wherein obtaining the plurality of raw signals comprises:
receiving reflected ultrasound energy from each of the transmitted ultrasound signals; and,
converting the reflected ultrasound energy from each of the transmitted ultrasound signals into the plurality of raw signals.

5. The method according to claim 3, wherein transmitting the ultrasound signals comprises:
transmitting a plurality of ultrasound pulses each having a frequency; and,
changing the frequency of the ultrasound pulses as the raw signals are acquired.

6. The method according to claim 5, wherein the frequency of the ultrasound pulses is changed by sweeping the frequency.

7. The method of claim 1, wherein generating the contour lines based on the peaks of the envelope signals comprises:
identifying a first peak of the one or more peaks in each envelope; and
applying a first filter to the first peaks in temporally adjacent envelopes.

8. The method according to claim 7, wherein the first peak is identified in each of the envelopes by using a second filter to estimate an optimal time delay.

9. The method according to claim 8, wherein the second filter is selected from a group consisting of a Kalman filter, a recursive Bayesian filter, and a particles filter.

10. The method according to claim 7, wherein the first filter is based on Bayesian model smoothing.

11. The method according to claim 1, wherein generating the contour lines based on the peaks of the envelopes comprises:
calculating a first peak data matrix for the envelope of a first raw signal of the plurality of raw signals;
estimating a second peak data matrix for the envelope of a second raw signal of the plurality of raw signals based on the first peak data matrix;
calculating the second peak data matrix from the envelope of the second raw signal;
calculating an error matrix based on a difference between the estimated second peak data matrix and the calculated second peak data matrix; and
calculating an error correction gain based on the error matrix.

12. The method according to claim 11, further comprising estimating a third peak data matrix for the envelope of a third raw signal of the plurality of raw signals by multiplying the error matrix by the error correction gain, and adding a product of the multiplication to the calculated second peak data matrix.

13. The method according to claim 1, wherein generating the contour lines based on the peaks of the envelopes comprises:
calculating a first peak data matrix for the envelope of a first raw signal of the plurality of raw signals;
generating a first set of particles for each peak in the first peak data matrix;
estimating a second peak data matrix for the envelope of a second raw signal of the plurality of raw signals based on the first set of particles for each peak in the first peak data matrix;
calculating a second peak data matrix for the envelope of the second raw signal;
calculating an error matrix based on a difference between the estimated second peak data matrix and the calculated second peak data matrix;
generating a second set of particles for each peak in the second peak data matrix; and
calculating a weight for each particle in the second set of particles for each peak in the second peak data matrix based on the error matrix.

14. The method according to claim 13, comprising estimating a third peak data matrix for the envelope of a third raw signal of the plurality of raw signals based on the weighted particles of the second set of particles for each peak in the second peak data matrix.

15. The method according to claim 12, wherein the first raw signal, the second raw signal, and the third raw signal are temporally adjacent raw signals.

16. The method according to claim 1, wherein transforming the contour lines into the 3-D point cloud includes extracting a 2-D feature from each contour line.

17. The method according to claim 1, wherein the contour lines are generated by:
applying a statistical weight to each of the one or more peaks in each of the envelopes to create weighted peaks; and
determining a path of each of the contour lines across the envelopes based on the weighted peaks.

18. An apparatus for generating a 3-D subject-specific musculoskeletal model, the apparatus comprising:
a processor; and
a memory containing instructions that, when executed by the processor, cause the apparatus to:
generate an envelope for each of a plurality of raw signals obtained from an ultrasound scan of at least a portion of a subject, each envelope including one or more peaks;
generate contour lines based on the peaks of the envelopes;
transform the contour lines into a three dimensional (3-D) point cloud using tracking information obtained by tracking a position of an ultrasound transducer during the ultrasound scan of at least the portion of the subject; and
optimize a template tissue model with respect to the point cloud to generate a virtual three dimensional subject-specific musculoskeletal model.

* * * * *